(12) United States Patent
Lang et al.

(10) Patent No.: US 6,358,286 B2
(45) Date of Patent: *Mar. 19, 2002

(54) COMPOSITION FOR THE OXIDATION DYEING OF KERATIN FIBRES AND DYEING PROCESS USING THIS COMPOSITION

(75) Inventors: Gérard Lang, Saint Prix; Jean Cotteret, Verneuil sur Seine, both of (FR)

(73) Assignee: L'Oreal S.A., Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/320,286

(22) Filed: May 26, 1999

(30) Foreign Application Priority Data

May 26, 1998 (FR) .............................. 98 06604

(51) Int. Cl.$^7$ .................................. A61K 7/13
(52) U.S. Cl. ................. 8/409; 8/407; 8/426; 8/654; 8/655; 8/657; 8/659; 8/406; 8/408; 8/410; 8/411; 8/412
(58) Field of Search .................... 8/426, 406, 407, 8/408, 409, 410, 411, 412, 657, 654, 655, 659

(56) References Cited

U.S. PATENT DOCUMENTS

| | | | | |
|---|---|---|---|---|
| 3,955,918 A | | 5/1976 | Lang ............................. | 8/426 |
| 3,985,499 A | | 10/1976 | Lang et al. .................... | 8/426 |
| 4,025,301 A | * | 5/1977 | Lang ............................. | 8/426 |
| 5,879,412 A | * | 3/1999 | Rondeau et al. ............... | 8/411 |
| 5,919,273 A | * | 7/1999 | Rondeau et al. ............... | 8/412 |
| 5,993,490 A | * | 11/1999 | Rondeau et al. ............... | 8/409 |
| 6,001,135 A | * | 12/1999 | Rondeau et al. ............... | 8/407 |

FOREIGN PATENT DOCUMENTS

| | | |
|---|---|---|
| DE | 2 359 399 | 6/1975 |
| DE | 3 843 892 | 6/1990 |
| DE | 4 133 957 | 4/1993 |
| DE | 195 43 988 | 5/1997 |
| EP | 0 770 375 | 5/1997 |
| EP | 0 850 636 | 7/1998 |
| EP | 0 850 637 | 7/1998 |
| EP | 0 850 638 | 7/1998 |
| FR | 2 140 205 | 1/1973 |
| FR | 2 189 006 | 1/1974 |
| FR | 2 282 860 | 3/1976 |
| FR | 2 586 913 | 3/1987 |
| FR | 2 733 749 | 11/1996 |
| FR | 2 750 048 | 12/1997 |
| GB | 1 026 978 | 4/1966 |
| GB | 1 153 196 | 5/1969 |
| JP | 9-110659 | 4/1997 |
| WO | WO 94/08969 | 4/1994 |
| WO | WO 94/08970 | 4/1994 |
| WO | WO 96/15765 | 5/1996 |

OTHER PUBLICATIONS

English language Derwent Abstract of DE 2 359 399, Jun. 1975.
English language Derwent Abstract of DE 3 843 892, Jun. 1990.
English language Derwent Abstract of DE 4 133 957, Apr. 1993.
English language Derwent Abstract of DE 195 43 988, May 1997.
English language Derwent Abstract of EP 0 850 636, Jul. 1998.
English language Derwent Abstract of EP 0 850 637, Jul. 1998.
English language Derwent Abstract of EP 0 850 638, Jul. 1998.
English language Derwent Abstract of FR 2 140 205, Jan. 1973.
English language Derwent Abstract of FR 2 189 006, Mar. 1974.
English language Derwent Abstract of FR 2 282 860, Mar. 1976.
English language Derwent Abstract of FR 2 586 913, Mar. 1987.
English language Derwent Abstract of FR 2 733 749, Nov. 1996.
English language Derwent Abstract of FR 2 750 048, Dec. 1997.
English language Derwent Abstract of JP 2019576, Jan. 1990.
English language Derwent Abstract of EP 0 770 375, May 1997.
English language Derwent Abstract of JP 9–110659, Apr. 1997.

* cited by examiner

*Primary Examiner*—Margaret Einsmann
(74) *Attorney, Agent, or Firm*—Finnegan, Henderson, Farabow, Garrett & Dunner L.L.P.

(57) ABSTRACT

The invention relates to a composition for the oxidation dyeing of keratin fibers, and in particular human keratin fibers such as the hair, having, in a medium suitable for dyeing, at least one oxidation base and at least one specific cationic dye as direct dye, as well as to the dyeing process using this composition.

49 Claims, No Drawings

COMPOSITION FOR THE OXIDATION DYEING OF KERATIN FIBRES AND DYEING PROCESS USING THIS COMPOSITION

The invention relates to a composition for the oxidation dyeing of keratin fibres, especially human keratin fibres such as the hair, comprising, in a medium suitable for dyeing, at least one oxidation base and at least one specific cationic dye as direct dye, as well as to the dyeing process using this composition.

It is known to dye keratin fibres, particularly human hair, with dye compositions containing oxidation dye precursors, in particular ortho- or para-phenylenediamines, ortho- or para-aminophenols and heterocyclic bases, generally referred to as oxidation bases. Oxidation dye precursors, or oxidation bases, are colourless or weakly coloured compounds which, when combined with oxidizing products, can give rise to coloured compounds and dyes by a process of oxidative condensation.

It is also known that the shades obtained with these oxidation bases can be varied by combining them with couplers or colour modifiers, the latter being chosen in particular from aromatic meta-diamines, meta-aminophenols, meta-diphenols and certain heterocyclic compounds.

The variety of compounds used as oxidation bases and couplers allows a wide range of colours to be obtained.

It is also known that direct dyes, i.e., coloured substances which give a coloration in the absence of an oxidizing agent, can be used, in combination with the oxidation dye precursors and the couplers, to further vary the shades obtained and to give them glints.

The vast majority of these direct dyes belong to the family of nitrobenzene compounds and have the drawback, when they are incorporated into dye compositions, of leading to colorations which show insufficient staying power, especially with respect to shampooing.

The so-called "permanent" coloration obtained by these oxidation dyes should, moreover, satisfy a certain number of objectives. The dyes should allow shades to be obtained in the desired intensity and should show good resistance to external agents (light, bad weather, washing, permanent-waving, perspiration, rubbing).

The dyes should also be able to cover grey hair and, finally, they should be as unselective as possible, ie., they should allow only the smallest possible colour differences along the same keratin fibre, which may indeed be differently sensitized, i.e., damaged, between its tip and its root.

The present invention is directed towards proposing novel compositions for the oxidation dyeing of keratin fibres, especially human keratin fibres such as the hair, which produce colorations that are preferably rich in glints while at the same time having good properties of staying power.

Thus, the inventors have discovered that it is possible to obtain novel dyes which are can be both rich in glints and have good staying power by combining:
 at least one oxidation base,
 at least one cationic direct dye of formula (I) defined below.

This discovery forms the basis of the present invention.

Additional features and advantages of the invention are set forth in the description that follows, and, in part, will be apparent from the description or may be learned from practice of the invention. The advantages of the invention will be realized and attained by the dyeing compositions, processes, and kits particularly pointed out in the written description and claims.

Both the foregoing general description and the following detailed description of the invention are exemplary and explanatory only and are not restrictive of the claimed invention.

A first subject of the invention is a composition for the oxidation dyeing of keratin fibres, especially human keratin fibres such as the hair, comprising, in a medium suitable for dyeing:
 at least one oxidation base,
 at least one cationic direct dye of formula (I) below:

$$A\text{—}N\text{=}N\text{—}B \qquad (I)$$

wherein:
A is chosen from structures A1, A2, and A3 below:

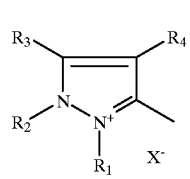

A1

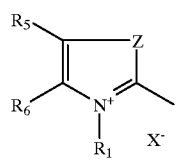

A2

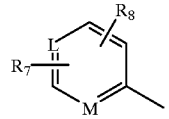

A3 wherein in said structures A1 to A3:
 $R_1$ is chosen from $C_1$–$C_4$ alkyl radicals, a phenyl radical, and phenyl radicals having a substituent chosen from $C_1$–$C_4$ alkyl radicals and halogen atoms chosen from chlorine, bromine, iodine and fluorine;
 $R_2$ is chosen from $C_1$–$C_4$ alkyl radicals and a phenyl radical;
 $R_3$ and $R_4$, which may be identical or different, are chosen from $C_1$–$C_4$ alkyl radicals and a phenyl radical or together form a benzene ring having at least one substituent chosen from $C_1$–$C_4$ alkyl radicals, $C_1$–$C_4$ alkoxy radicals, and nitro radicals; $R_3$ can also be a hydrogen atom;
 $R_5$ and $R_6$, which may be identical or different, are chosen from $C_1$–$C_4$ alkyl radicals and a phenyl radical or together form a benzene ring which is unsubstituted or has at least one substituent chosen from $C_1$–$C_4$ alkyl radicals, $C_1$–$C_4$ alkoxy radicals, and nitro radicals; $R_5$ can also be a hydrogen atom;
 $R_7$ and $R_8$, which may be identical or different, are chosen from a hydrogen atom, halogen atoms chosen from chlorine, bromine, iodine and fluorine, $C_1$–$C_4$ alkyl radicals, $C_1$–$C_4$ alkoxy radicals and nitro radicals;
 Z is chosen from an oxygen atom, a sulphur atom, and a group $NR_2$, wherein $R_2$ is chosen from $C_1$–$C_4$ alkyl radicals and a phenyl radical;
 the ring member L is chosen from —CH, —CR and —N$^+$R$_9$(X$^-$)$_r$;

the ring member M is chosen from —CH, —CR and —N⁺R₉(X⁻)ᵣ;
r is an integer equal to 0 or 1;
R is chosen from $C_1$–$C_4$ alkyl radicals;
$R_9$ is chosen from an atom $O^-$, $C_1$–$C_4$ alkyl radicals, and $C_1$–$C_4$ alkoxy radicals;
$X^-$ is chosen from an anion preferably chloride, methyl sulphate, ethyl sulphate, acetate, and perchlorate;
with the provisos that:
in the formula A3, at least one of the ring members L and M is chosen from a group —N⁺R₉(X⁻)ᵣ;
when $R_6$ is a $C_1$–$C_4$ alkyl radical and Z is a sulphur atom, then $R_5$ is other than a $C_1$–$C_4$ alkyl radical;
when $R_6$ is a $C_1$–$C_4$ alkyl radical and Z is a sulphur atom and when one of the radicals $R_{10}$ and $R_{11}$, defined below, is a hydrogen atom, then $R_5$ is other than a hydrogen atom;
when $R_9$ is $O^-$, then r=0;
when L or M is a radical —N⁺R₉(X⁻)ᵣ wherein $R_9$ is a $C_1$–$C_4$ alkyl radical and r=1, then at least one of the radicals $R_7$ and $R_8$ is other than a hydrogen atom;
when L is a radical —N⁺R₉(X⁻)ᵣ, then M is chosen from a group —CH and CR;
when M is a radical —N⁺R₉(X⁻)ᵣ, then L is chosen from a group —CH and CR;
when Z is a group $NR_2$ wherein $R_2$ is a $C_1$–$C_4$ alkyl radical, then at least one of the radicals $R_1$, $R_5$ and $R_6$ is other than a $C_1$–$C_4$ alkyl radical;
when Z is a sulphur atom and $R_1$ is a $C_1$–$C_4$ alkyl radical and when one of the radicals $R_{10}$ and $R_{11}$, defined below, is a hydrogen atom, then $R_5$ and $R_6$ cannot together form an unsubstituted benzene ring;
B is chosen from:
(a) a group of structure B1 below:

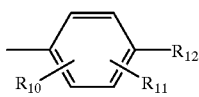

B1 wherein in structure B1,
$R_{10}$ is chosen from a hydrogen atom, halogen atoms chosen from chlorine, bromine, iodine and fluorine, $C_1$–$C_4$ alkyl radicals, $C_1$–$C_4$ alkoxy radicals, a hydroxyl radical, —$NHR_{13}$ groups, —$NR_{14}R_{15}$ groups, —$NHCO(C_1$–$C_4)$alkyl groups and a nitro, or forms with $R_{11}$ a 5- or 6-membered carbon ring or a ring containing at least one hetero atom chosen from nitrogen, oxygen and sulphur;
$R_{11}$ is chosen from a hydrogen atom, halogen atoms chosen from chlorine, bromine, iodine and fluorine, $C_1$–$C_4$ alkyl radicals, and $C_1$–$C_4$ alkoxy radicals or forms with $R_{12}$ or $R_{13}$ a 5- or 6-membered carbon ring or a ring containing at least one hetero atom chosen from nitrogen, oxygen and sulphur;
$R_{12}$ is chosen from a hydrogen atom, a hydroxyl radical, —$NHR_{13}$ radicals, and —$NR_{14}R_{15}$ radicals;
$R_{13}$ is chosen from a hydrogen atom, $C_1$–$C_4$ alkyl radicals, $C_1$–$C_4$ monohydroxyalkyl radicals, $C_2$–$C_4$ polyhydroxyalkyl radicals, and a phenyl radical;

$R_{14}$ and $R_{15}$, which may be identical or different, are chosen from $C_2$–$C_4$ alkyl radicals, $C_1$–$C_4$ monohydroxyalkyl radicals, and $C_2$–$C_4$ polyhydroxyalkyl radicals; and
(b) a 5- or 6-membered nitrogenous heterocyclic group, a 5- or 6-membered nitrogenous heterocyclic group comprising at least one additional hetero atom chosen from oxygen and sulphur and/or at least one carbonyl group, wherein said heterocycles are unsubstituted or have at least one substituent chosen from $C_1$–$C_4$ alkyl, amino and phenyl radicals.

Among the said 5- or 6-membered nitrogenous heterocyclic groups featured above, preferred compounds include groups of structure B2 below:

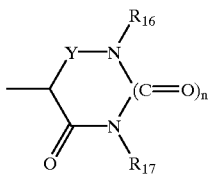

B2 wherein in structure B2:
$R_{16}$ and $R_{17}$, which may be identical or different, are chosen from a hydrogen atom, $C_1$–$C_4$ alkyl radicals and a phenyl radical;
Y is chosen from

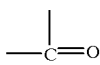

and

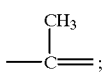

and
n is an integer equal to 0 or 1.

The cationic direct dyes of formula (I) above are known compounds of the prior art and are described, for example, in patent application FR-A-2,140,205 and its Certificates of Addition, as well as in patent application FR-A-2,189,006, the disclosures of which are specifically incorporated by reference herein.

The dye composition according to the invention can give intense, chromatic colorations which show little selectivity and excellent properties of resistance both with respect to atmospheric agents such as light and bad weather, and with respect to perspiration and the various treatments to which hair may be subjected. These properties can be particularly noteworthy with respect to chromaticity.

Another subject of the invention is a process for the oxidation dyeing of keratin fibres using this dye composition.

In the compounds of formula (I) above, the $C_1$–$C_4$ alkyl and alkoxy radicals are preferably chosen from the methyl, ethyl, butyl, methoxy and ethoxy radicals.

The nature of the oxidation base(s) used in the dye composition according to the invention is not a critical factor. They can be chosen, for example, from para-phenylenediamines, double bases, para-aminophenols, ortho-aminophenols and heterocyclic oxidation bases.

Among the para-phenylenediamines which can be used as oxidation bases in the dye compositions according to the invention, examples include the compounds of formula (II) below, and the addition salts thereof with an acid:

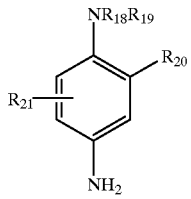

(II)

wherein:
- $R_{18}$ is chosen from a hydrogen atom, $C_1$–$C_4$ alkyl radicals, $C_1$–$C_4$ monohydroxyalkyl radicals, $C_2$–$C_4$ polyhydroxyalkyl radicals, ($C_1$–$C_4$)alkoxy($C_1$–$C_4$)alkyl radicals, $C_1$–$C_4$ alkyl radicals substituted with an entity chosen from nitrogenous groups, a phenyl group and a 4'-aminophenyl group;
- $R_{19}$ is chosen from a hydrogen atom, $C_1$–$C_4$ alkyl radicals, $C_1$–$C_4$ monohydroxyalkyl radicals, $C_2$–$C_4$ polyhydroxyalkyl radicals, ($C_2$–$C_4$)alkoxy($C_1$–$C_4$)alkyl radicals and $C_1$–$C_4$ alkyl radicals substituted with a nitrogenous group;
- $R_{20}$ is chosen from a hydrogen atom, halogen atoms such as chlorine, bromine, iodine and fluorine atoms, $C_1$–$C_4$ alkyl radicals, $C_1$–$C_4$ monohydroxyalkyl radicals, $C_1$–$C_4$ hydroxyalkoxy radicals, acetylamino($C_1$–$C_4$) alkoxy radicals, $C_1$–$C_4$ mesylaminoalkoxy radicals and carbamoylamino($C_1$–$C_4$)alkoxy radicals,
- $R_{21}$ is chosen from hydrogen and halogen atoms and $C_1$–$C_4$ alkyl radicals.

Among the nitrogenous groups of formula (II) above, examples include amino, mono($C_1$–$C_4$)alkylamino, di($C_1$–$C_4$)alkylamino, tri($C_1$–$C_4$)alkylamino, monohydroxy($C_1$–$C_4$)alkylamino, imidazolinium and ammonium radicals.

Among the para-phenylenediamines of formula (II) above, examples include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(βγ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine and N-(β-methoxyethyl)-para-phenylenediamine, and the acid addition salts thereof.

Among the para-phenylenediamines of formula (II) above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the acid addition salts thereof, are most particularly preferred.

According to the invention, the term double bases is understood to refer to the compounds comprising at least two aromatic rings bearing amino and/or hydroxyl groups.

Among the double bases which can be used as oxidation bases in the dye compositions according to the invention, examples include the compounds corresponding to formula (III) below, and the acid addition salts thereof:

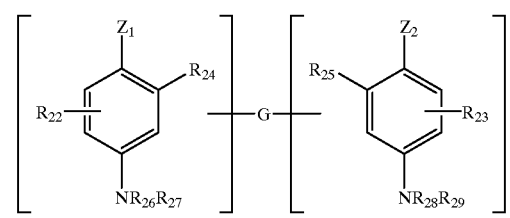

(III)

wherein:
- $Z_1$ and $Z_2$, which may be identical or different, are chosen from a hydroxyl radical and an —$NH_2$ radical which may be substituted with a $C_1$–$C_4$ alkyl radical or with a linker arm G;
- the linker arm G is chosen from linear alkylene chains comprising from 1 to 14 carbon atoms and branched alkylene chains comprising from 2 to 14 carbon atoms, wherein said chains may be interrupted by or terminated with at least one nitrogenous group and/or at least one hetero atom, such as oxygen, sulphur and nitrogen atoms, and optionally substituted with at least one radical chosen from hydroxyl and $C_1$–$C_6$ alkoxy radicals;
- $R_{22}$ and $R_{23}$ are chosen from hydrogen and halogen atoms, $C_1$–$C_4$ alkyl radicals, $C_1$–$C_4$ monohydroxyalkyl radicals, $C_2$–$C_4$ polyhydroxyalkyl radicals, $C_1$–$C_4$ aminoalkyl radicals, and a linker arm G;
- $R_{24}$, $R_{25}$, $R_{26}$, $R_{27}$, $R_{28}$ and $R_{29}$, which may be identical or different, are chosen from a hydrogen atom, a linker arm G and $C_1$–$C_4$ alkyl radicals;

with the proviso that the compounds of formula (III) contain only one linker arm G per molecule.

Among the nitrogenous groups of formula (III) above, examples include amino, mono($C_1$–$C_4$)alkylamino, di($C_1$–$C_4$)alkylamino, tri($C_1$–$C_4$)alkylamino, monohydroxy($C_1$–$C_4$)alkylamino, imidazolinium and ammonium radicals.

Among the double bases of formula (III) above, examples include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl)-tetramethylenediamine, N,N'-bis(4-methylaminophenyl) tetramethylenediamine, N,N'-bis-(ethyl)-N,N'-bis(4'-amino-3'-methylphenyl)ethylenediamine and 1,8-bis(2,5diaminophenoxy)-3,5-dioxaoctane, and the acid addition salts thereof.

Among these double bases of formula (III), N,N'-bis(β-hydroxyethyl)-N,N'-bis(4'-aminophenyl)-1,3- diaminopropanol and 1,8-bis(2,5-diaminophenoxy)-3,5-dioxaoctane, or one of the acid addition salts thereof, are particularly preferred.

Among the para-aminophenols which can be used as oxidation bases in the dye compositions according to the invention, examples include the compounds corresponding to formula (IV) below, and the acid addition salts thereof:

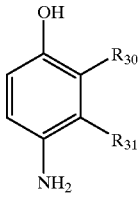

(IV)

wherein:
- $R_{30}$ is chosen from hydrogen and halogen atoms, $C_1$–$C_4$ alkyl radicals, $C_1$–$C_4$ monohydroxyalkyl radicals, $(C_1$–$C_4)$alkoxy$(C_1$–$C_4)$alkyl radicals, $C_1$–$C_4$ aminoalkyl radicals, and hydroxy$(C_1$–$C_4)$alkylamino $(C_1$–$C_4)$alkyl radicals,
- $R_{31}$ is chosen from hydrogen and halogen atoms, $C_1$–$C_4$-alkyl radicals, $C_1$–$C_4$ monohydroxyalkyl radicals, $C_2$–$C_4$ polyhydroxyalkyl radicals, $C_1$–$C_4$ aminoalkyl radicals, $C_1$–$C_4$ cyanoalkyl radicals, and $(C_1$–$C_4)$ alkoxy-$(C_1$–$C_4)$alkyl radicals, with the proviso that at least one of the radicals $R_{30}$ and $R_{31}$ is a hydrogen atom.

Among the para-aminophenols of formula (IV) above, examples include para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the acid addition salts thereof.

Among the ortho-aminophenols which can be used as oxidation bases in the dye compositions according to the invention, examples include 2-aminophenol, 2-amino-5-methylphenol, 2-amino-6-methylphenol and 5-acetamido-2-aminophenol, and the acid addition salts thereof.

Among the heterocyclic bases which can be used as oxidation bases in the dye compositions according to the invention, examples include pyridines, pyrimidines and pyrazoles, and the acid addition salts thereof.

Among the pyridines, preferred compounds are described, for example, in patents GB 1,026,978 and GB 1,153,196 (the disclosures of which are specifically incorporated by reference herein), such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the acid addition salts thereof.

Among the pyrimidines, preferred compounds are described, for example, in German patent DE 2,359,399 or Japanese patents JP 88-169,571 and JP 91-10659 or patent application WO 96/15765 (the disclosures of which are specifically incorporated by reference herein), such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2,750,048 (the disclosure of which is specifically incorporated by reference herein), and examples include pyrazolo[1,5-a]pyrimidine-3,7-diamine; 2,5-dimethylpyrazolo[1,5-a]pyrimidine-3,7-diamine, pyrazolo[1,5-a]pyrimidine-3,5-diamine; 2,7-dimethylpyrazolo[1,5-a]pyrimidine-3,5-diamine, 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine and 2,5,N7,N7-tetramethylpyrazolo[1,5-a]pyrimidine-3,7-diamine and the addition salts and tautomeric forms thereof, when a tautomeric equilibrium exists, and the acid addition salts thereof.

Among the pyrazoles, preferred compounds are described in patents DE 3,843,892, DE 4,133,957 and patent applications WO 94/08969, WO 94/08970, FR-A-2,733,749 and DE 195 43 988 (the disclosures of which are specifically incorporated by reference herein), for example 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the acid addition salts thereof.

The at least one oxidation base preferably is present in an amount ranging from about 0.0005 to about 12% by weight relative to the total weight of the dye composition according to the invention, and even more preferably from about 0.005 to about 6% by weight relative to this weight.

The preferred at least one cationic direct dye of formula (I) according to the invention is chosen from:

4'-dimethylaminophenyl-2-azopyridine N-oxide of formula:

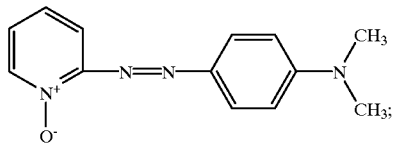

4'-dimethylamino-2'-methylphenyl-2-azopyridine N-oxide of formula:

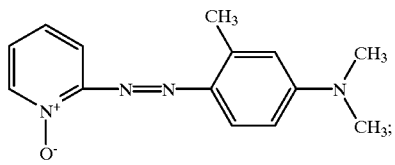

2-[(1,3-diamino-6-methyl-4-phenyl)azo]-3-methylbenzothiazolium iodide of formula:

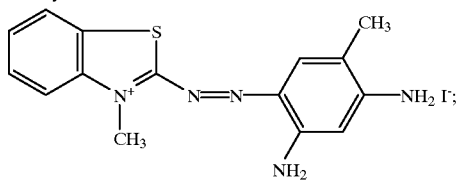

6'-hydroxybenzomorpholine-7'-aza-2-methyl-3-benzothiazolium chloride of formula:

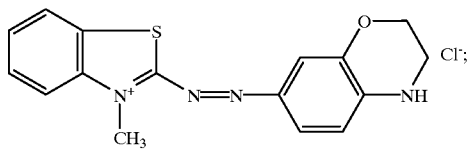

6'-hydroxybenzomorpholine-7'-aza-2-methyl-4-phenyl-3-thiazolium perchlorate of formula:

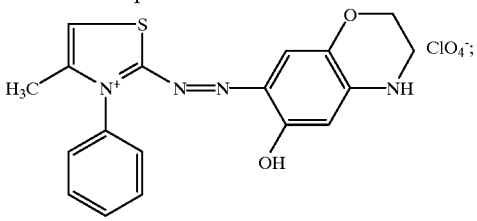

6'-hydroxybenzomorpholine-7'-azo-2-diphenyl-3,4-thiazolium perchlorate of formula:

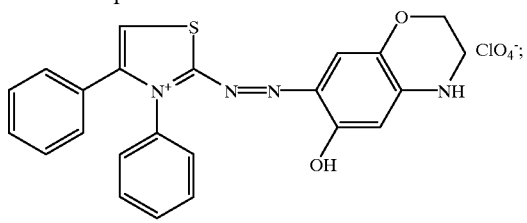

6'-hydroxybenzomorpholine-7'-aza-2-methyl-3-benzothiazolium chloride of formula:

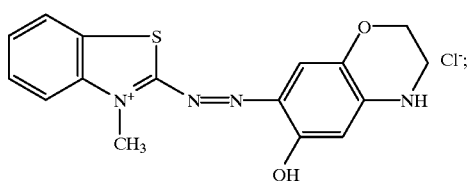

6'-hydroxybenzomorpholine-7'-aza-2-methyl-4-phenyl-3-thiazolium perchlorate of formula:

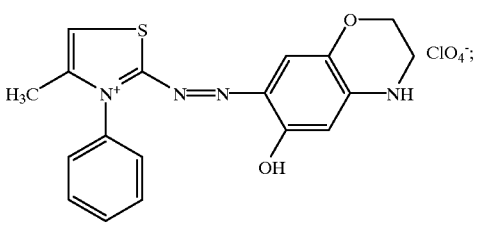

2',4'-diamino-5'-methoxyphenyl-2-azopyridine N-oxide of formula:

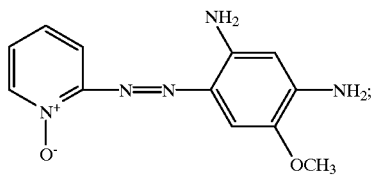

2'-acetamido-4'-hydroxy-5'-methylphenyl-2-azopyridine N-oxide of formula:

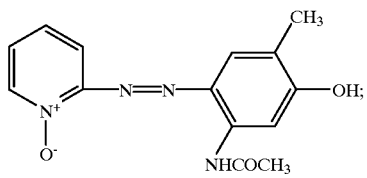

2'-acetamido-4'-dimethylaminophenyl-2-azopyridine N-oxide of formula:

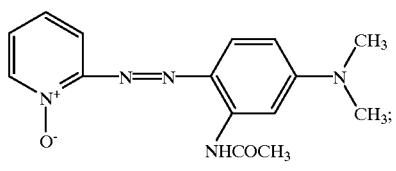

2'-amino-4'-dimethylaminophenyl-2-azopyridine N-oxide of formula:

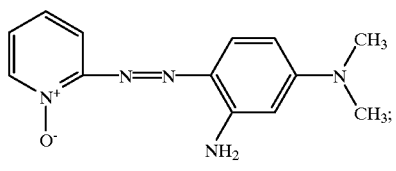

2',4'-diamino-5'-methylphenyl-2-azomethoxy-1-pyridinium perchlorate of formula:

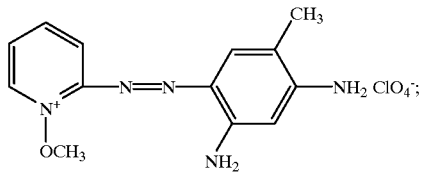

2',5'-dimethyl-4'-hydroxyphenyl-2-azopyridine N-oxide of formula:

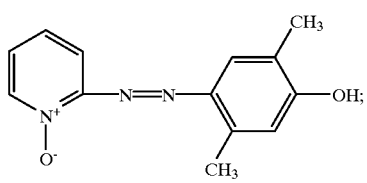

2'-dimethylamino-4'-hydroxyphenyl-2-azopyridine N-oxide of formula:

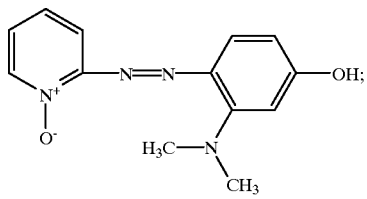

4'-dimethylamino-2'-hydroxyphenyl-2-azopyridine N-oxide of formula:

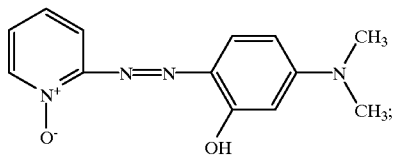

3',5'-dimethyl-4'-hydroxyphenyl-2-azopyridine N-oxide of formula:

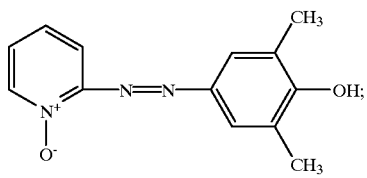

4'-dimethylamino-2'-nitrophenyl-2-azopyridine N-oxide of formula:

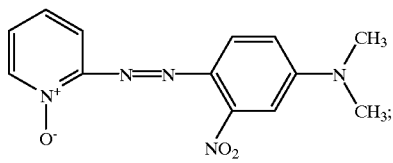

8'-hydroxyquinoline-5':2'-azopyridine N-oxide of formula:

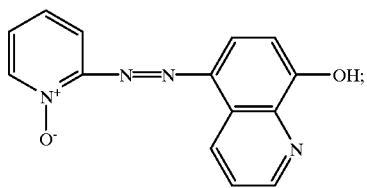

2'-nitro-4'-dimethylaminophenyl-2-azomethoxy-1-pyridinium methosulphate of formula:

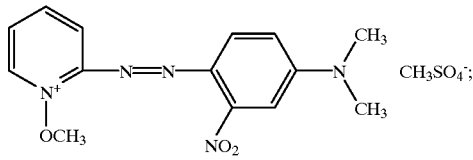

4'-dimethylaminophenyl-2-azo-5-nitropyridine N-oxide of formula:

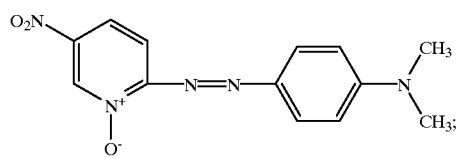

4'-dimethylaminophenyl-2-azo-6-methylpyridine N-oxide of formula:

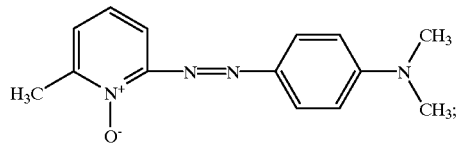

4'-dimethylaminophenyl-2-azo-5-methylpyridine N-oxide of formula:

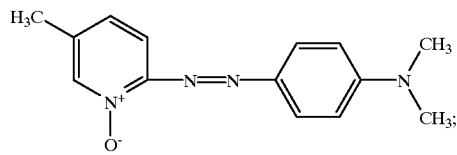

4'-dimethylaminophenyl-2-azo-3-methylpyridine N-oxide of formula:

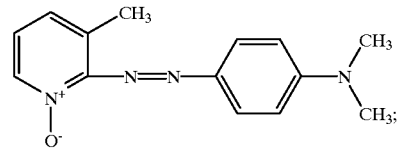

4'-diethylaminophenyl-2-azo-3-methylpyridine N-oxide of formula:

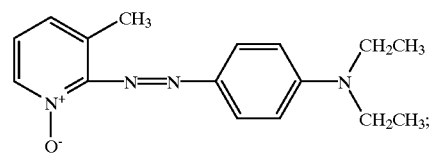

4'-dimethylamino-2'-acetylaminophenyl-2-azo-3-methylpyridine N-oxide of formula:

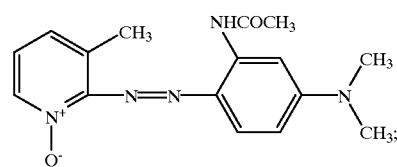

4'-aminonaphthalene-1':2-azo-6-methylpyridine N-oxide of formula:

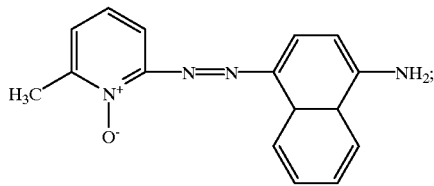

4'-di(β-hydroxyethyl)aminophenyl-2-azo-6-methylpyridine N-oxide of formula:

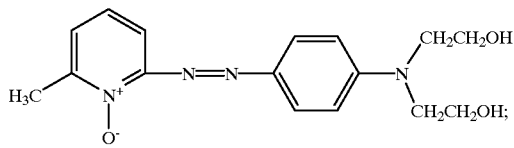

4'-diethylaminophenyl-2-azo-6-methylpyridine N-oxide of formula:

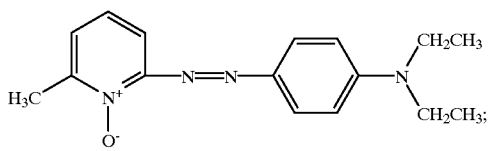

2',5'-dimethyl-4'-hydroxyphenyl-2-azo-6-methylpyridine N-oxide of formula:

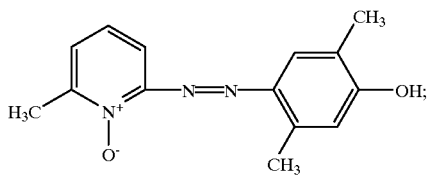

4'-di(β-hydroxyethyl)aminophenyl-2-azo-4-methylpyridine N-oxide of formula:

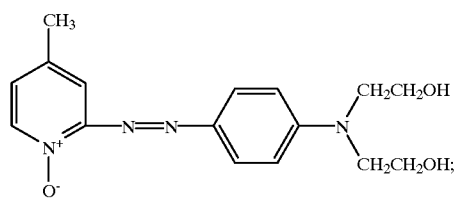

4'-diethylaminophenyl-2-azo-4-methylpyridine N-oxide of formula:

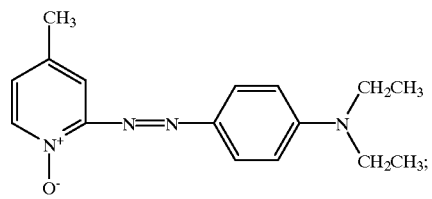

4'-aminonaphthalene-1':2-azo-4-methylpyridine N-oxide of formula:

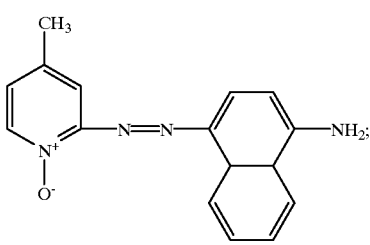

2',4'-diamino-5'-methylphenyl-2-azo-2-4-methylpyridine N-oxide of formula:

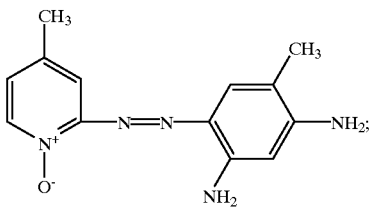

4'-dimethylaminophenyl-2-azo-4-methylpyridine N-oxide of formula:

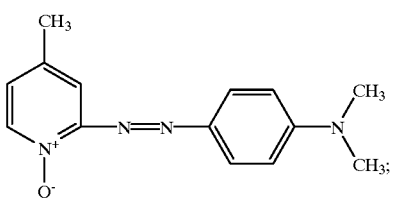

4'-dimethylaminophenyl-2-azo-4,6-dimethylpyridine N-oxide of formula:

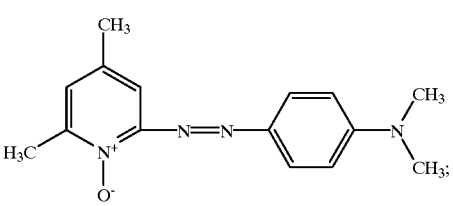

2',5'-dimethyl-4'-hydroxyphenyl-2-azo-4-methylpyridine N-oxide of formula:

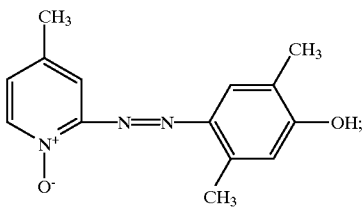

4'-dimethylaminophenyl-2-azo-5-chloropyridine N-oxide of formula:

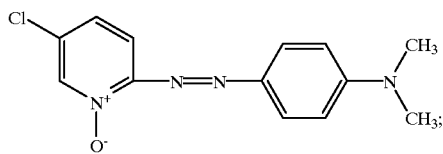

4'-dimethylamino-2'-methylphenyl-2-azo-5-chloropyridine N-oxide of formula:

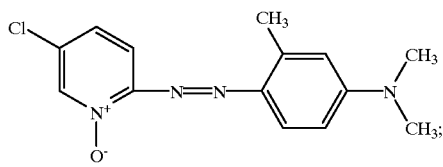

4'-diethylaminophenyl-2-azo-5-chloropyridine N-oxide of formula:

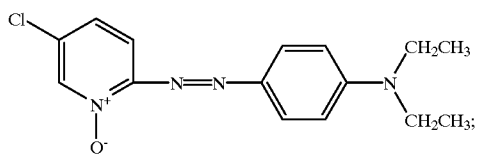

6'-hydroxybenzomorpholine-7':2-azopyridine N-oxide of formula:

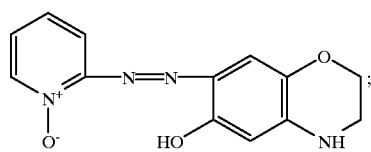

6'-hydroxybenzomorpholine-7':2-azo-1-methoxypyridinium methosulphate of formula:

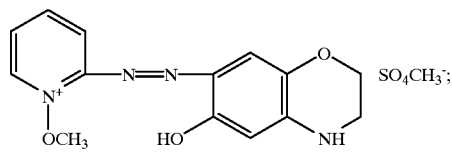

2',4'-diamino-5'-methylphenyl-2-azopyridine N-oxide of formula:

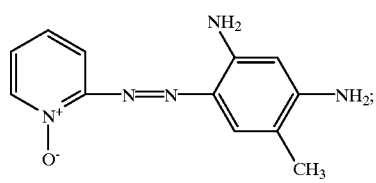

2'-methyl-5'-oxo-4'-phenyidihydropyrazolyl-2-azo-1-methoxypyridinium methosulphate of formula:

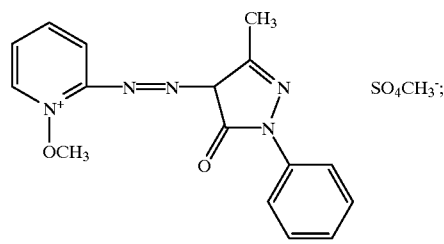

3'-methyl-2',4',6'-trioxohexahydropyrimidinyl-2-azopyridine N-oxide of formula:

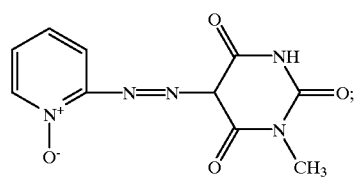

4'-aminophenyl-2-azopyridine N-oxide of formula:

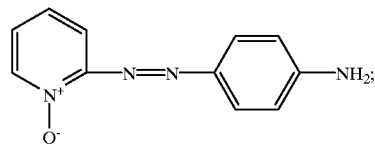

4'-di(β-hydroxyethyl)aminophenyl-2-azopyridine N-oxide of formula:

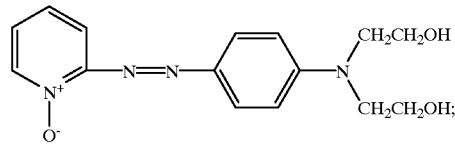

4'-(N-phenylamino)phenyl-2-azopyridine N-oxide of formula:

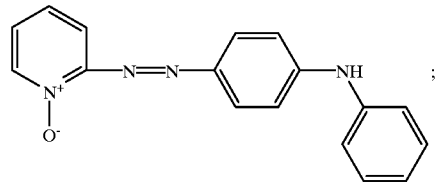

4'-(N-phenylamino)phenyl-2-azo-3-methylpyridine N-oxide of formula:

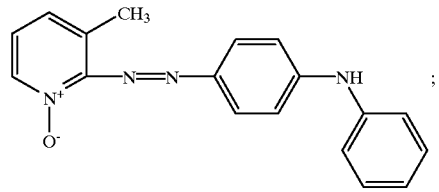

4'-aminophenyl-2-azo-1,3-dimethylpyridinium methosulphate of formula:

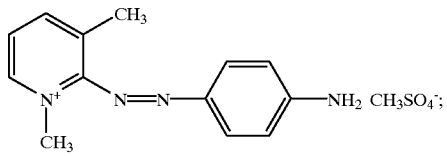

4'-di(β-hydroxyethyl)aminophenyl-2-azo-1,4-dimethylpyridinium methosulphate of formula:

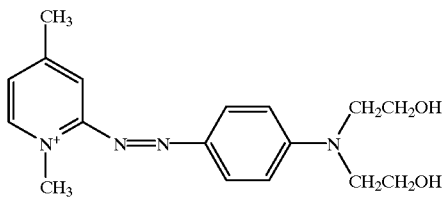

4'-dimethylaminophenyl-2-azo-1,3-dimethylpyridinium methosulphate of formula:

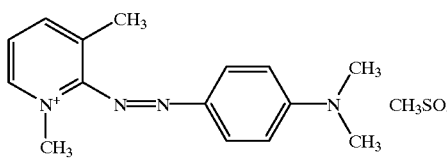

4'-N-phenylaminophenyl-2-azo-1,6-dimethylpyridinium methosulphate of formula:

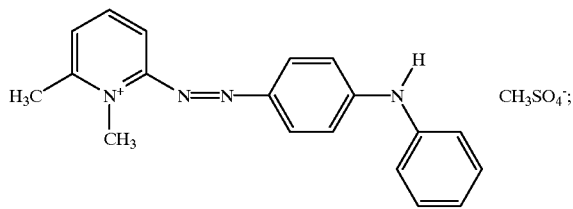

4'-dimethylaminophenyl-2-azo-1,5-dimethylpyridinium methosulphate of formula:

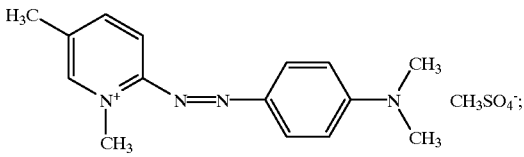

4'-dimethylaminophenyl-2-azo-1,6-dimethylpyridinium methosulphate of formula:

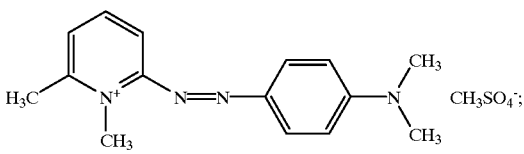

2',4',6'-trioxohexahydropyrimidinyl-2-azopyridine N-oxide of formula:

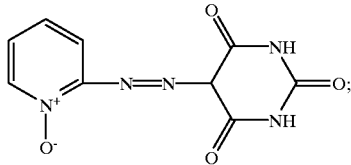

4'-dimethylaminophenyl-2-azo-1,3-dimethylbenzimidazolium perchlorate of formula:

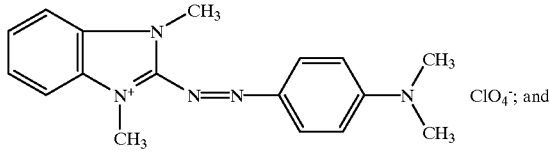

2',4'-diamino-3'-pyridine-2-azopyridine N-oxide of formula:

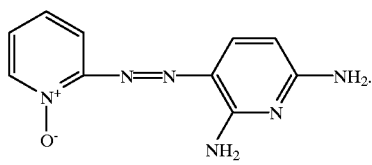

The at least one cationic direct dye of formula (I) used according to the invention preferably is present in an amount ranging from about 0.001 to about 10% by weight relative to the total weight of the dye composition, and even more preferably from about 0.01 to about 5% by weight relative to this weight.

The dye composition according to the invention may further comprise at least one coupler and/or at least one additional direct dye other than the compounds of formula (I), particularly to modify the shades or to enrich them with glints.

Among the couplers which can be present in the dye composition according to the invention, examples include meta-phenylenediamines, meta-aminophenols, meta-diphenols and heterocyclic couplers, and the addition salts thereof with an acid.

When they are present, the at least one coupler preferably is present in an amount ranging from about 0.0001 to about 10% by weight relative to the total weight of the dye composition, and even more preferably from about 0.005 to about 5% by weight relative to this weight.

In general, the preferred addition salts with an acid which can be used in the context of the dye compositions of the invention (oxidation bases and couplers) are the hydrochlorides, hydrobromides, sulphates, tartrates, lactates and acetates.

The medium suitable for dyeing (or support) for the dye composition according to the invention generally comprises water or a mixture of water and at least one organic solvent to dissolve the compounds which would not be sufficiently water-soluble. Examples include $C_1$–$C_4$ alkanols, such as ethanol and isopropanol, as organic solvents.

The solvents can be present in proportions preferably ranging from about 1 to about 40% by weight relative to the total weight of the dye composition, and even more preferably from about 5 to about 30% by weight.

The pH of the dye composition according to the invention generally ranges from about 3 to about 12, and preferably from about 5 to about 12. The pH can be adjusted to the desired value by means of acidifying or basifying agents usually used for dyeing keratin fibres.

Representative acidifying agents include organic or inorganic acids such as hydrochloric acid, orthophosphoric acid, sulphuric acid, carboxylic acids such as acetic acid, tartaric acid, citric acid and lactic acid, and sulphonic acids.

Representative basifying agents include aqueous ammonia, alkaline carbonates, alkanolamines such as mono-, di- and triethanolamine, 2-methyl-2-aminopropanol and derivatives thereof, sodium hydroxide, potassium hydroxide and the compounds of formula (IX) below:

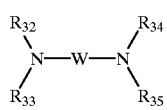

(V)

wherein W is a propylene residue optionally substituted with a hydroxyl group or a $C_1$–$C_4$ alkyl radical; $R_{32}$, $R_{33}$, $R_{34}$ and $R_{35}$, which may be identical or different, are chosen from a hydrogen atom and $C_1$–$C_4$ alkyl and $C_1$–$C_4$ hydroxyalkyl radicals.

The dye composition according to the invention can also contain various adjuvants conventionally used in compositions for dyeing the hair.

Needless to say, a person skilled in the art will take care to select this or these optional complementary compounds such that the advantageous properties intrinsically associated with the dye composition according to the invention are not, or are not substantially, adversely affected by the addition(s) envisaged.

The dye composition according to the invention can be in various forms, such as in the form of liquids, creams or gels, which may be pressurized, or in any other form suitable for dyeing keratin fibres, particularly human hair.

Another subject of the invention is a process for dyeing keratin fibres, especially human keratin fibres such as the hair, using the dye composition as defined above.

According to this process, the dye composition as defined above is applied to the fibres, the colour being developed at acidic, neutral or alkaline pH by means of an oxidizing agent added to the dye composition just at the time of use, or which is present in an oxidizing composition applied simultaneously or sequentially in a separate manner.

According to one particularly preferred embodiment of the dyeing process according to the invention, the dye composition described above is mixed, at the time of use, with an oxidizing composition containing, in a medium suitable for dyeing, at least one oxidizing agent present in an amount sufficient to develop a coloration. The mixture obtained is then applied to the keratin fibres and is left on the fibres for about 3 to about 50 minutes, preferably for about 5 to about 30 minutes, after which the fibres are rinsed, washed with shampoo, rinsed again and dried.

The oxidizing agent present in the oxidizing composition as defined above can be chosen from the oxidizing agents conventionally used for the oxidation dyeing of keratin fibres, such as, for example, hydrogen peroxide, urea peroxide, alkali metal bromates, persalts such as perborates and persulphates, peracids, and enzymes such as 2-electron oxidoreductases, peroxidases and lactases. Hydrogen peroxide is particularly preferred.

The pH of the oxidizing composition containing the oxidizing agent as defined above is such that, after mixing with the dye composition, the pH of the resulting composition applied to the keratin fibres preferably ranges from about 3 to about 12 and even more preferably from about 5 to about 11. The pH is adjusted to the desired value by means of acidifying or basifying agents usually used for dyeing keratin fibres and as defined above.

The oxidizing composition as defined above can also contain various adjuvants conventionally used in compositions for dyeing the hair.

The composition that is finally applied to the keratin fibres can be in various forms, such as in the form of liquids, creams or gels or in any other form suitable for dyeing keratin fibres, particularly human hair.

Another subject of the invention is a multi-compartment dyeing device or "kit" or any other multi-compartment packaging system, a first compartment comprising the dye composition as defined above and a second compartment comprising the oxidizing composition as defined above. These devices can be equipped with means for delivering the desired mixture onto the hair, such as the devices described in patent FR-2,586,913, in the name of the L'Oréal, the disclosure of which is specifically incorporated by reference herein.

The present invention is further illustrated by the following examples which are designed to teach those of ordinary skill in the art how to practice the invention. The following examples are intended to illustrate the invention without limiting its scope.

EXAMPLES

Dyeing Examples 1 to 4

The dye compositions below, according to the invention, were prepared (contents in grams):

| EXAMPLE | 1 | 2 | 3 | 4 |
|---|---|---|---|---|
| 4'-Dimethylaminophenyl-2-azopyridine N-oxide (compound of formula (I)) | 0.5 | — | 4.0 | — |
| 4'-Dimethylaminophenyl-2-azo-1,3-dimethylpyridinium methosulphate (compound of formula (I)) | — | 0.5 | — | 4.0 |
| para-Phenylenediamine (oxidation base) | 0.324 | 0.324 | 0.324 | 0.324 |
| 5-Amino-2-methylphenol (coupler) | 0.369 | — | 0.369 | — |
| meta-Aminophenol (coupler) | — | 0.327 | — | 0.327 |
| Common dye support | (*) | (*) | (*) | (*) |
| Demineralized water qs | 100 g | 100 g | 100 g | 100 g |

| (*): Common dye support: | |
|---|---|
| Oleyl alcohol polyglycerolated with 2 mol of glycerol | 4.0 g |
| Oleyl alcohol polyglycerolated with 4 mol of glycerol, containing 78% active material (A.M.) | 5.69 g A.M. |
| Oleic acid | 3.0 g |
| Oleylamine containing 2 mol of ethylene oxide, sold under the trade name Ethomeen O12 ® by the company Akzo | 7.0 g |
| Diethylaminopropyl laurylaminosuccinamate, sodium salt, containing 55% A.M. | 3.0 g A.M. |
| Oleyl alcohol | 5.0 g |
| Oleic acid diethanolamide | 12.0 g |
| Propylene glycol | 3.5 g |
| Ethyl alcohol | 16.5 g |
| Sodium metabisulphite as an aqueous solution containing 35% A.M. | 0.455 g A.M. |
| Ammonium acetate | 0.8 g |
| Antioxidant, sequestering agent | q.s. |
| Fragrance, preserving agent | q.s. |
| Aqueous ammonia containing 20% $NH_3$ | 10.0 g |

Each of the dye compositions described above was mixed, at the time of use, with an equivalent amount by weight of 20-volumes hydrogen peroxide (6% by weight) with a pH of about 3.

Each resulting mixture had a pH of about 10±0.2 and was applied for 30 minutes to locks of grey hair containing 90% permanent-waved white hairs.

The locks were then rinsed with water, washed with a standard shampoo, rinsed again and then dried.

The hair was dyed in the shades featured in the table below:

| EXAMPLE | SHADE OBTAINED |
|---------|----------------|
| 1 | Intense red |
| 2 | Intense purple |
| 3 | Intense red |
| 4 | Intense purple |

The foregoing written description relates to various embodiments of the present invention. Numerous changes and modifications may be made therein without departing from the spirit and scope of the invention as defined in the following claims.

What is claimed is:

1. A composition for the oxidation dyeing of keratin fibres comprising:
   at least one oxidation base,
   at least one cationic direct dye of formula (I) below:

wherein:
   A is chosen from structures A1, A2, and A3 below:

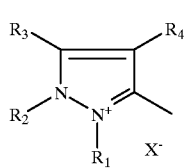

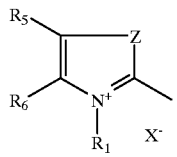

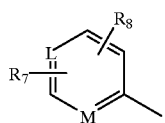

wherein in said structures A1 to A3:
   $R_1$ is chosen from $C_1$–$C_4$ alkyl radicals, a phenyl radical, and phenyl radicals having a substituent chosen from $C_1$–$C_4$ alkyl radicals and halogen atoms chosen from chlorine, bromine, iodine and fluorine;
   $R_2$ is chosen from $C_1$–$C_4$ alkyl radicals and a phenyl radical;
   $R_3$ and $R_4$, which may be identical or different, are chosen from $C_1$–$C_4$ alkyl radicals and a phenyl radical or together form a benzene ring having at least one substituent chosen from $C_1$–$C_4$ alkyl radicals, $C_1$–$C_4$ alkoxy radicals, and nitro radicals; $R_3$ can also be a hydrogen atom;
   $R_5$ and $R_6$, which may be identical or different, are chosen from $C_1$–$C_4$ alkyl radicals and a phenyl radical or together form a benzene ring which is unsubstituted or has at least one substituent chosen from $C_1$–$C_4$ alkyl radicals, $C_1$–$C_4$ alkoxy radicals, and nitro radicals; $R_5$ can also be a hydrogen atom;
   $R_7$ and $R_8$, which may be identical or different, are chosen from a hydrogen atom, halogen atoms chosen from chlorine, bromine, iodine and fluorine, $C_1$–$C_4$ alkyl radicals, $C_1$–$C_4$ alkoxy radicals and nitro radicals;
   Z is chosen from an oxygen atom, a sulphur atom, and a group $NR_2$, wherein $R_2$ is chosen from $C_1$–$C_4$ alkyl radicals and a phenyl radical;
   the ring member L is chosen from —CH, —CR and —$N^+R_9(X^-)_r$;
   the ring member M is chosen from —CH, —CR and —$N^+R_9(X^-)_r$;
   r is an integer equal to 0 or 1;
   R is chosen from $C_1$–$C_4$ alkyl radicals;
   $R_9$ is chosen from an atom $O^-$, $C_1$–$C_4$ alkyl radicals, and $C_1$–$C_4$ alkoxy radicals;
   $X^-$ is chosen from an anion;
   with the provisos that:
   in said structure A3, at least one of the ring members L and M is a group —$N^+R_9(X^-)_r$;
   when $R_6$ is a $C_1$–$C_4$ alkyl radical and Z is a sulphur atom, then $R_5$ is other than a $C_1$–$C_4$ alkyl radical;
   when $R_9$ is $O^-$, then r=0;
   when L or M is a radical —$N^+R_9(X^-)_r$ wherein $R_9$ is a $C_1$–$C_4$ alkyl radical and r=1, then at least one of the radicals $R_7$ and $R_8$ is other than a hydrogen atom;
   when L is a radical —$N^+R_9(X^-)_r$, then M is chosen from —CH and CR;
   when M is a radical —$N^+R_9(X^-)_r$, then L is chosen from —CH and CR;
   when Z is a group $NR_2$ wherein $R_2$ is a $C_1$–$C_4$ alkyl radical, then at least one of the radicals $R_1$, $R_5$ and $R_6$ is other than a $C_1$–$C_4$ alkyl radical;
   B is chosen from:
   (a) a group of structure B1 below:

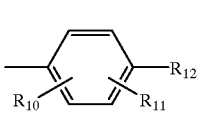

wherein in structure B1,
   $R_{10}$ is chosen from a hydrogen atom, halogen atoms chosen from chlorine, bromine, iodine and fluorine, $C_1$–$C_4$ alkyl radicals, $C_1$–$C_4$ alkoxy radicals, a hydroxyl radical, —$NHR_{13}$ groups, —$NR_{14}R_{15}$ groups, —$NHCO(C_1$–$C_4)$alkyl groups and a nitro, or forms with $R_{11}$ a 5- or 6-membered carbon ring or a ring containing at least one hetero atom chosen from nitrogen, oxygen and sulphur;
   $R_{11}$ is chosen from a hydrogen atom, halogen atoms chosen from chlorine, bromine, iodine and fluorine, $C_1$–$C_4$ alkyl radicals, and $C_1$–$C_4$ alkoxy radicals or forms with $R_{12}$ or $R_{13}$ a 5- or 6-membered carbon ring or a ring containing at least one hetero atom chosen from nitrogen, oxygen and sulphur;

R$_{12}$ is chosen from a hydrogen atom, a hydroxyl radical, —NHR$_{13}$ radicals, and —NR$_{14}$R$_{15}$ radicals;

R$_{13}$ is chosen from a hydrogen atom, C$_1$–C$_4$ alkyl radicals, C$_1$–C$_4$ monohydroxyalkyl radicals, C$_2$–C$_4$ polyhydroxyalkyl radicals, and a phenyl radical;

R$_{14}$ and R$_{15}$, which may be identical or different, are chosen from C$_1$–C$_4$ alkyl radicals, C$_1$–C$_4$ monohydroxyalkyl radicals, and C$_2$–C$_4$ polyhydroxyalkyl radicals;

with the provisos that when Z in structure A2 is a sulphur atom and R$_1$ is a C$_1$–C$_4$ alkyl radical and when one of the radicals R$_{10}$ and R$_{11}$ in structure B1 is a hydrogen atom, then R$_5$ and R$_6$ cannot together form an unsubstituted benzene ring and when R$_6$ in structure A2 is a C$_1$–C$_4$ alkyl radical and Z is a sulphur atom and when one of the radicals R$_{10}$ and R$_{11}$ in structure B1 is a hydrogen atom, then R$_5$ is other than a hydrogen atom; and (b) a 5- or 6-membered nitrogenous heterocyclic group, a 5- or 6-membered nitrogenous heterocyclic group comprising at least one additional hetero atom chosen from oxygen and sulphur and/or at least one carbonyl group, wherein said heterocycles are unsubstituted or have at least one substituent chosen from C$_1$–C$_4$ alkyl, amino and phenyl radicals.

2. A composition according to claim 1, wherein said keratin fibres are human keratin fibres.

3. A composition according to claim 2, wherein said human keratin fibres are human hair.

4. A composition according to claim 1, having a pH ranging from 3 to 12.

5. A composition according to claim 1, having a pH ranging from about 3 to about 12.

6. A composition according to claim 5, wherein said pH ranges from about 5 to about 11.

7. A composition according to claim 1, wherein said anion X$^-$ is chosen from chloride, methyl sulphate, ethyl sulphate, acetate, and perchlorate.

8. A composition according to claim 1, wherein in said B, said 5- or 6-membered nitrogenous heterocyclic group is a group of structure B2 below:

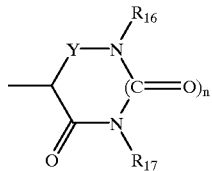

B2 wherein structure B2:

R$_{16}$ and R$_{17}$ are identical or different and are chosen from a hydrogen atom, C$_1$–C$_4$ alkyl radicals and a phenyl radical;

Y is chosen from a group

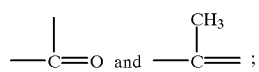

and n is an integer equal to 0 or 1.

9. A composition according to claim 1, wherein said at least one oxidation base is chosen from para-phenylenediamines, double bases, para-aminophenols, ortho-aminophenols, and heterocyclic oxidation bases.

10. A composition according to claim 9, wherein said para-phenylenediamines are chosen from compounds of formula (II) below and acid addition salts thereof:

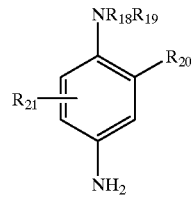

(II)

wherein:

R$_{18}$ is chosen from a hydrogen atom, C$_1$–C$_4$ alkyl radicals, C$_1$–C$_4$ monohydroxyalkyl radicals, C$_2$–C$_4$ polyhydroxyalkyl radicals, (C$_1$–C$_4$)alkoxy(C$_1$–C$_4$) alkyl radicals, C$_1$–C$_4$ alkyl radicals substituted with an entity chosen from nitrogenous groups, a phenyl group and a 4'-aminophenyl group;

R$_{19}$ is chosen from a hydrogen atom, C$_1$–C$_4$ alkyl radicals, C$_1$–C$_4$ monohydroxyalkyl radicals, C$_2$–C$_4$ polyhydroxyalkyl radicals, (C$_1$–C$_4$)alkoxy(C$_1$–C$_4$) alkyl radicals and C$_1$–C$_4$ alkyl radicals substituted with a nitrogenous group;

R$_{20}$ is chosen from a hydrogen atom, halogen atoms, C$_1$–C$_4$ alkyl radicals, C$_1$–C$_4$ monohydroxyalkyl radicals, C$_1$–C$_4$ hydroxyalkoxy radicals, acetylamino (C$_1$–C$_4$)alkoxy radicals, C$_1$–C$_4$ mesylaminoalkoxy radicals and carbamoylamino(C$_1$–C$_4$)alkoxy radicals, R$_{21}$ is chosen from hydrogen and halogen atoms and C$_1$–C$_4$ alkyl radicals.

11. A composition according to claim 10, wherein said halogen atoms are chosen from chlorine, bromine, iodine, and fluorine atoms.

12. A composition according to claim 10, wherein said para-phenylenediamines of formula (II) are chosen from para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and acid addition salts thereof.

13. A composition according to claim 9, wherein said double bases are chosen from compounds of formula (III) below and acid addition salts thereof:

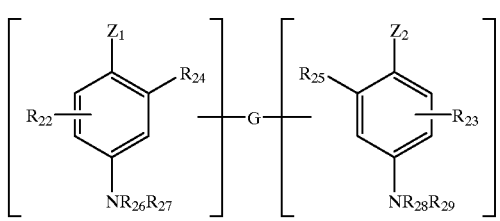

(III)

wherein:
- $Z_1$ and $Z_2$, which may be identical or different, are chosen from a hydroxyl radical and an —$NH_2$ radical which may be substituted with a $C_1$–$C_4$ alkyl radical or with a linker arm G;
- the linker arm G is chosen from linear alkylene chains comprising from 1 to 14 carbon atoms and branched alkylene chains comprising from 2 to 14 carbon atoms, wherein said chains may be interrupted by or terminated with at least one nitrogenous group and/or at least one hetero atom and optionally substituted with at least one radical chosen from hydroxyl and $C_1$–$C_6$ alkoxy radicals;
- $R_{22}$ and $R_{23}$ are chosen from hydrogen and halogen atoms, $C_1$–$C_4$ alkyl radicals, $C_1$–$C_4$ monohydroxyalkyl radicals, $C_2$–$C_4$ polyhydroxyalkyl radicals, $C_1$–$C_4$ aminoalkyl radicals, and a linker arm G;
- $R_{24}$, $R_{25}$, $R_{26}$, $R_{27}$, $R_{28}$ and $R_{29}$, which may be identical or different, are chosen from a hydrogen atom, a linker arm G and $C_1$–$C_4$ alkyl radicals;

with the proviso that the compounds of formula (III) contain only one linker arm G per molecule.

14. A composition according to claim 13, wherein said at least one hetero atom in said linker arm G is chosen from oxygen, sulphur, and nitrogen atoms.

15. A composition according to claim 13, wherein said double bases of formula (III) are chosen from N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and acid addition salts thereof.

16. A composition according to claim 9, wherein said para-aminophenols are chosen from compounds of formula (IV) below and acid addition salts thereof:

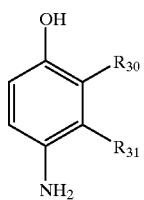

(IV)

wherein:
- $R_{30}$ is chosen from hydrogen and halogen atoms, $C_1$–$C_4$ alkyl radicals, $C_1$–$C_4$ monohydroxyalkyl radicals, ($C_1$–$C_4$)alkoxy($C_1$–$C_4$)alkyl radicals, $C_1$–$C_4$ aminoalkyl radicals, and hydroxy($C_1$–$C_4$)alkylamino ($C_1$–$C_4$)alkyl radicals, —$R_{31}$ is chosen from hydrogen and halogen atoms, $C_1$–$C_4$-alkyl radicals, $C_1$–$C_4$ monohydroxyalkyl radicals, $C_2$–$C_4$ polyhydroxyalkyl radicals, $C_1$–$C_4$ aminoalkyl radicals, $C_1$–$C_4$ cyanoalkyl radicals, and ($C_1$–$C_4$)alkoxy-($C_1$–$C_4$)alkyl radicals, with the proviso that at least one of the radicals $R_{30}$ and $R_{31}$ is a hydrogen atom.

17. A composition according to claim 16, wherein said para-aminophenols of formula (IV) are chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and acid addition salts thereof.

18. A composition according to claim 9, wherein said ortho-aminophenols are chosen from 2-aminophenol, 2-amino-5-methylphenol, 2-amino-6-methylphenol, 5-acetamido-2-aminophenol, and acid addition salts thereof.

19. A composition according to claim 9, wherein said heterocyclic oxidation bases are chosen from pyridines, pyrimidines, pyrazoles, and acid addition salts thereof.

20. A composition according to claim 1, wherein said at least one oxidation base is present in an amount ranging from about 0.0005 to about 12% by weight relative to the total weight of the dye composition.

21. A composition according to claim 20, wherein said at least one oxidation base is present in an amount ranging from about 0.005 to about 6% by weight relative to the total weight of the dye composition.

22. A composition according to claim 1, wherein said at least one cationic direct dye of formula (I) is chosen from:

4'-dimethylaminophenyl-2-azopyridine N-oxide of formula:

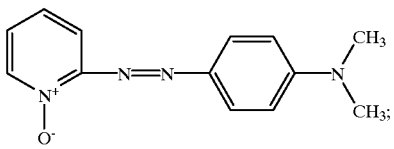

4'-dimethylamino-2'-methylphenyl-2-azopyridine N-oxide of formula:

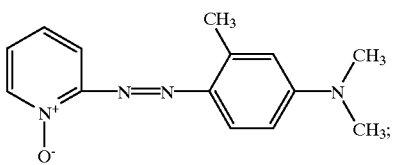

2-[(1,3-diamino-6-methyl-4-phenyl)azo]-3-methylbenzothiazolium iodide of formula:

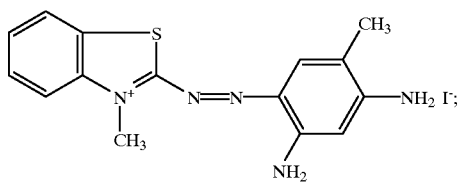

6'-hydroxybenzomorpholine-7'-aza-2-methyl-3-benzothiazolium chloride of formula:

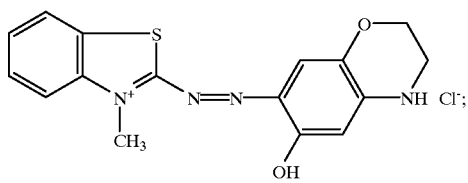

6'-hydroxybenzomorpholine-7'-aza-2-methyl-4-phenyl-3-thiazolium perchlorate of formula:

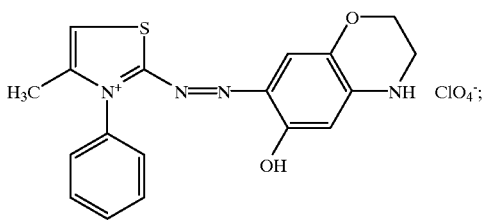

6'-hydroxybenzomorpholine-7'-azo-2-diphenyl-3,4-thiazolium perchlorate of formula:

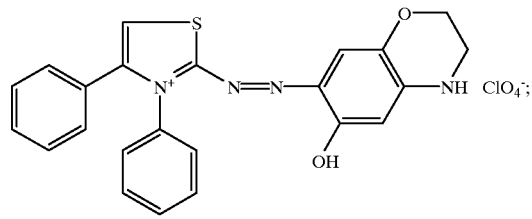

6'-hydroxybenzomorpholine-7'-aza-2-methyl-3-benzothiazolium chloride of formula:

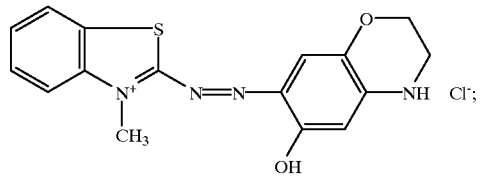

6'-hydroxybenzomorpholine-7'-aza-2-methyl-4-phenyl-3-thiazolium perchlorate of formula:

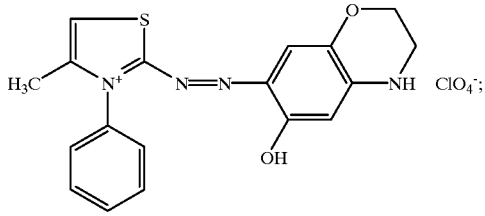

2',4'-diamino-5'-methoxyphenyl-2-azopyridine N-oxide of formula:

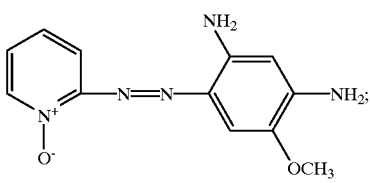

2'-acetamido-4'-hydroxy-5'-methylphenyl-2-azopyridine N-oxide of formula:

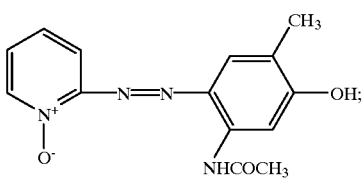

2'-acetamido-4'-dimethylaminophenyl-2-azopyridine N-oxide of formula:

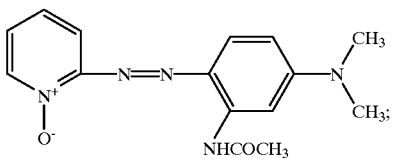

2'-amino-4'-dimethylaminophenyl-2-azopyridine N-oxide of formula:

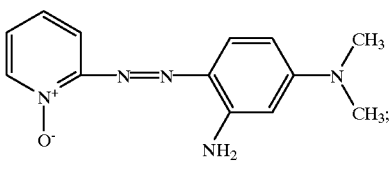

2',4'-diamino-5'-methylphenyl-2-azomethoxy-1-pyridinium perchlorate of formula:

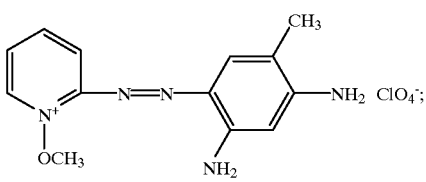

2',5'-dimethyl-4'-hydroxyphenyl-2-azopyridine N-oxide of formula:

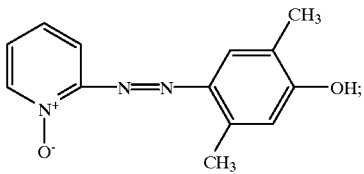

2'-dimethylamino-4'-hydroxyphenyl-2-azopyridine N-oxide of formula:

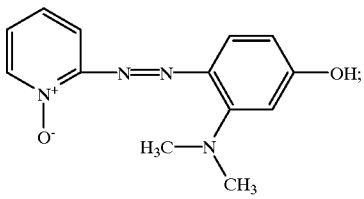

4'-dimethylamino-2'-hydroxyphenyl-2-azopyridine N-oxide of formula:

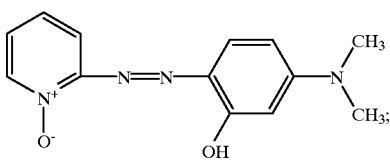

3',5'-dimethyl-4'-hydroxyphenyl-2-azopyridine N-oxide of formula:

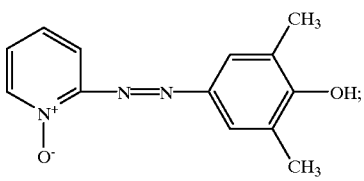

4'-dimethylamino-2'-nitrophenyl-2-azopyridine N-oxide of formula:

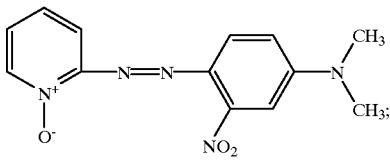

8'-hydroxyquinoline-5':2'-azopyridine N-oxide of formula:

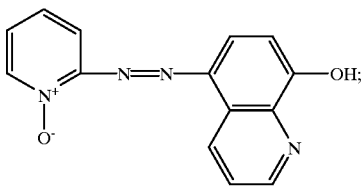

2'-nitro-4'-dimethylaminophenyl-2-azomethoxy-1-pyridinium methosulphate of formula:

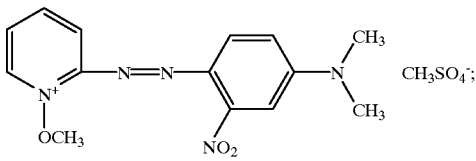

4'-dimethylaminophenyl-2-azo-5-nitropyridine N-oxide of formula:

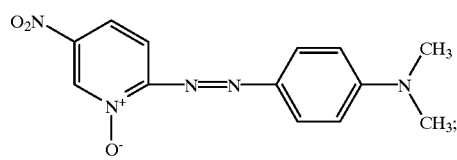

4'-dimethylaminophenyl-2-azo-6-methylpyridine N-oxide of formula:

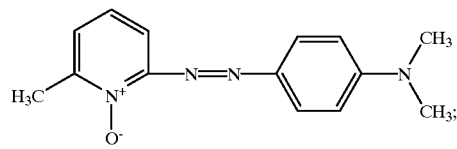

4'-dimethylaminophenyl-2-azo-5-methylpyridine N-oxide of formula:

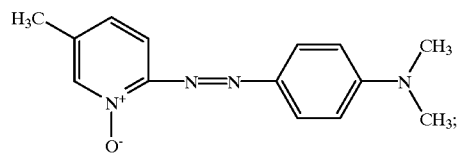

4'-dimethylaminophenyl-2-azo-3-methylpyridine N-oxide of formula:

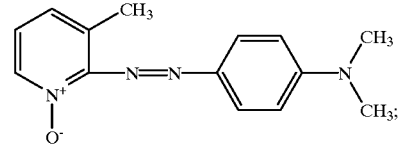

4'-diethylaminophenyl-2-azo-3-methylpyridine N-oxide of formula:

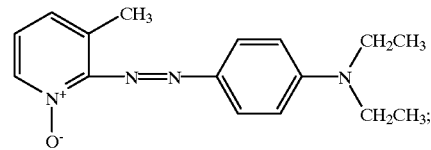

4'-dimethylamino-2'-acetylaminophenyl-2-azo-3-methylpyridine N-oxide of formula:

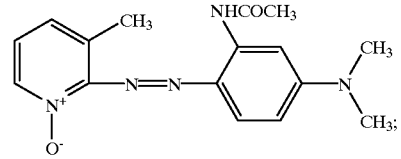

4'-aminonaphthalene-1':2-azo-6-methylpyridine N-oxide of formula:

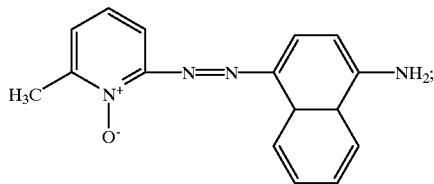

4'-di(β-hydroxyethyl)aminophenyl-2-azo-6-methylpyridine N-oxide of formula:

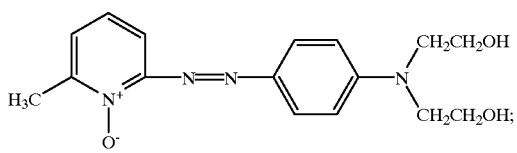

4'-diethylaminophenyl-2-azo-6-methylpyridine N-oxide of formula:

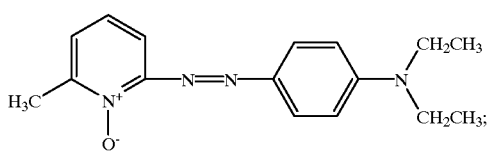

2',5'-dimethyl-4'-hydroxyphenyl-2-azo-6-methylpyridine N-oxide of formula:

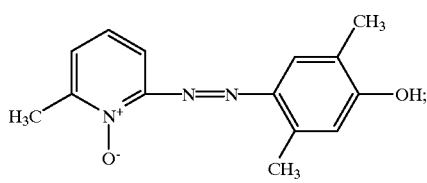

4'-di(β-hydroxyethyl)aminophenyl-2-azo-4-methylpyridine N-oxide of formula:

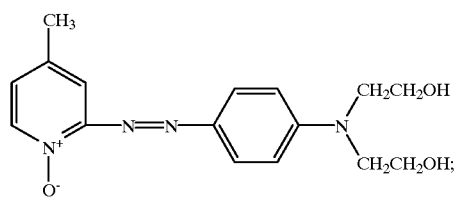

4'-diethylaminophenyl-2-azo-4-methylpyridine N-oxide of formula:

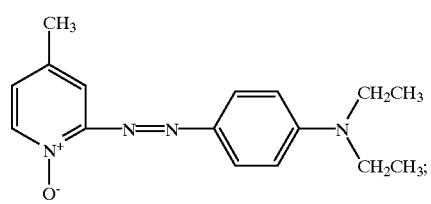

4'-aminonaphthalene-1':2-azo-4-methylpyridine N-oxide of formula:

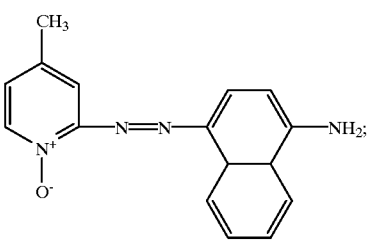

2',4'-diamino-5'-methylphenyl-2-azo-2-4-methylpyridine N-oxide of formula:

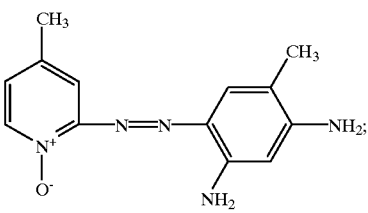

4'-dimethylaminophenyl-2-azo-4-methylpyridine N-oxide of formula:

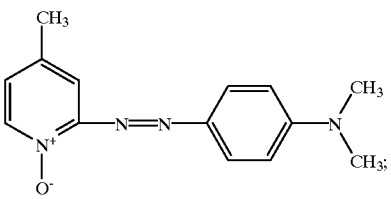

4'-dimethylaminophenyl-2-azo-4,6-dimethylpyridine N-oxide of formula:

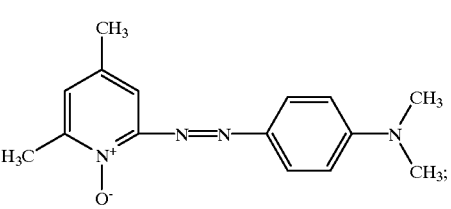

2',5'-dimethyl-4'-hydroxyphenyl-2-azo-4-methylpyridine N-oxide of formula:

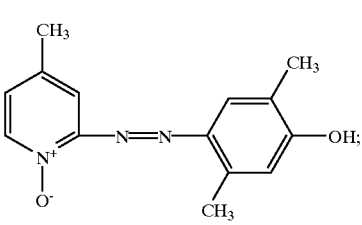

4'-dimethylaminophenyl-2-azo-5-chloropyridine N-oxide of formula:

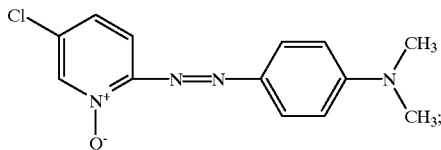

4'-dimethylamino-2'-methylphenyl-2-azo-5-chloropyridine N-oxide of formula:

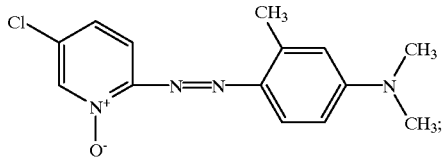

4'-diethylaminophenyl-2-azo-5-chloropyridine N-oxide of formula:

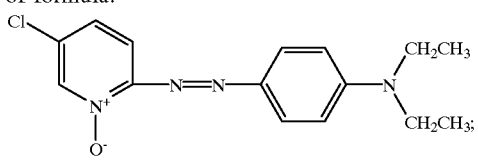

6'-hydroxybenzomorpholine-7':2-azopyridine N-oxide of formula:

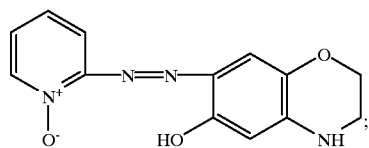

6'-hydroxybenzomorpholine-7':2-azo-1-methoxypyridinium methosulphate of formula:

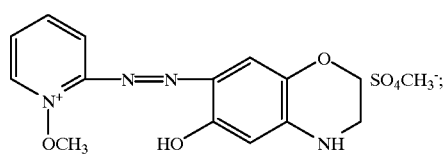

2',4'-diamino-5'-methylphenyl-2-azopyridine N-oxide of formula:

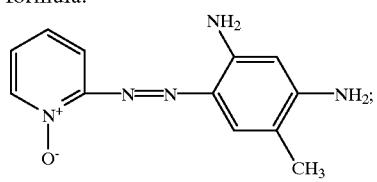

2'-methyl-5'-oxo-4'-phenyldihydropyrazolyl-2-azo-1-methoxypyridinium methosulphate of formula:

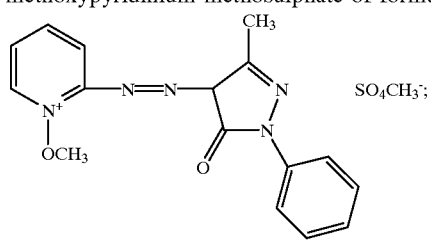

3'-methyl-2',4',6'-trioxohexahydropyrimidinyl-2-azopyridine N-oxide of formula:

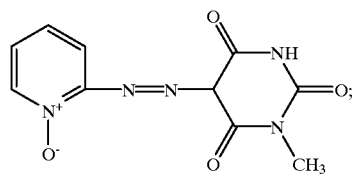

4'-aminophenyl-2-azopyridine N-oxide of formula:

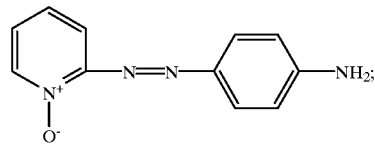

4'-di(β-hydroxyethyl)aminophenyl-2-azopyridine N-oxide of formula:

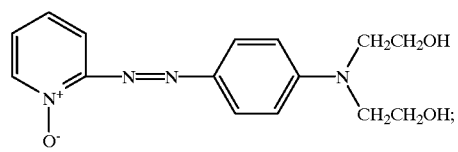

4'-(N-phenylamino)phenyl-2-azopyridine N-oxide of formula:

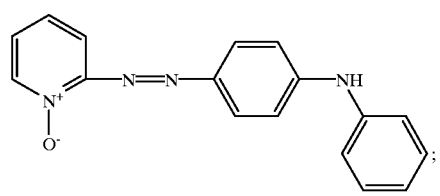

4'-(N-phenylamino)phenyl-2-azo-3-methylpyridine N-oxide of formula:

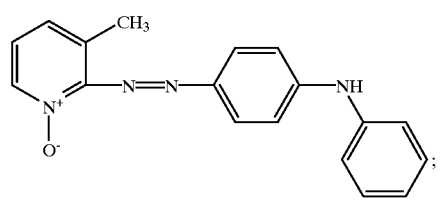

4'-aminophenyl-2-azo-1,3-dimethylpyridinium methosulphate of formula:

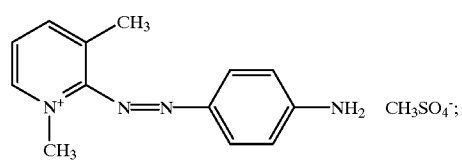

4'-di(β-hydroxyethyl)aminophenyl-2-azo-1,4-dimethylpyridinium methosulphate of formula:

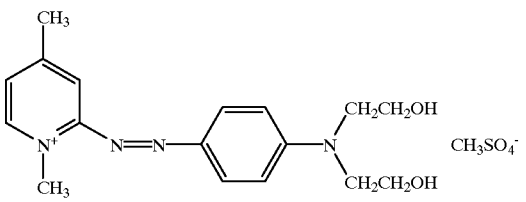

4'-dimethylaminophenyl-2-azo-1,3-dimethylpyridinium methosulphate of formula:

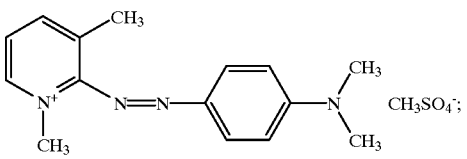

4'-N-phenylaminophenyl-2-azo-1,6-dimethylpyridinium methosulphate of formula:

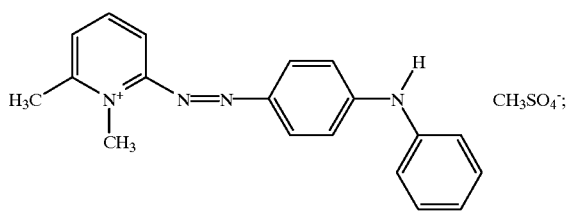

4'-dimethylaminophenyl-2-azo-1,5-dimethylpyridinium methosulphate of formula:

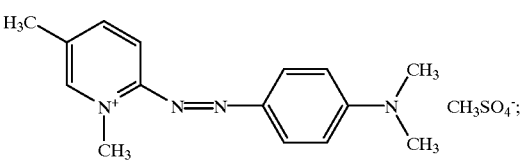

4'-dimethylaminophenyl-2-azo-1,6-dimethylpyridinium methosulphate of formula:

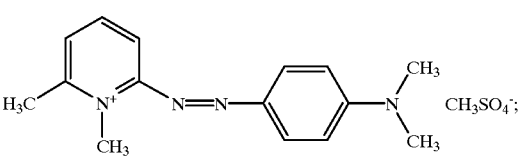

2',4',6'-trioxohexahydropyrimidinyl-2-azopyridine N-oxide of formula:

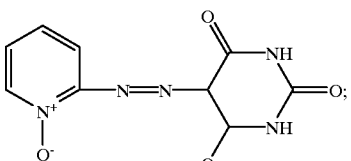

4'-dimethylaminophenyl-2-azo-1,3-dimethylbenzimidazolium perchlorate of formula:

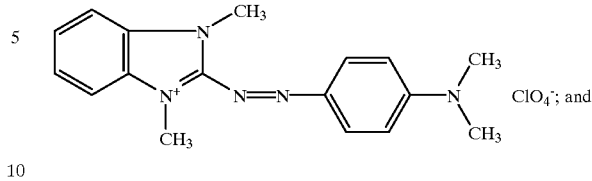

2',4'-diamino-3'-pyridine-2-azopyridine N-oxide of formula:

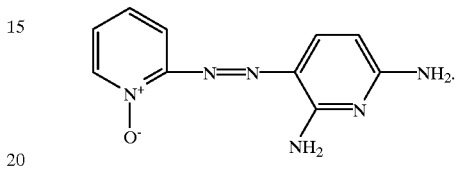

23. A composition according to claim 1, wherein said at least one cationic direct dye of formula (I) is present in an amount ranging from about 0.001 to about 10% by weight relative to the total weight of the dye composition.

24. A composition according to claim 23, wherein said at least one cationic direct dye of formula (I) is present in an amount ranging from about 0.01 to about 5% by weight relative to the total weight of the dye composition.

25. A composition according to claim 1, further comprising at least one ingredient chosen from couplers and direct dyes other than said at least one cationic direct dye of formula (I).

26. A composition according to claim 25, wherein said couplers are chosen from meta-phenylenediamines, meta-aminophenols, meta-diphenols, heterocyclic couplers, and acid addition salts thereof.

27. A composition according to claim 25, wherein said at least one ingredient is chosen from couplers and is present in an amount ranging from about 0.0001 to about 10% by weight relative to the total weight of the dye composition.

28. A composition according to claim 27, wherein said at least one ingredient is chosen from couplers and is present in an amount ranging from about 0.005 to about 5% by weight relative to the total weight of the dye composition.

29. A composition according to claim 10, wherein said acid addition salts are chosen from hydrochloride, hydrobromide, sulphate, tartrate, lactate, and acetate.

30. A composition according to claim 12, wherein said acid addition salts are chosen from hydrochloride, hydrobromide, sulphate, tartrate, lactate, and acetate.

31. A composition according to claim 13, wherein said acid addition salts are chosen from hydrochloride, hydrobromide, sulphate, tartrate, lactate, and acetate.

32. A composition according to claim 15, wherein said acid addition salts are chosen from hydrochloride, hydrobromide, sulphate, tartrate, lactate, and acetate.

33. A composition according to claim 16, wherein said acid addition salts are chosen from hydrochloride, hydrobromide, sulphate, tartrate, lactate, and acetate.

34. A composition according to claim 17, wherein said acid addition salts are chosen from hydrochloride, hydrobromide, sulphate, tartrate, lactate, and acetate.

35. A composition according to claim 18, wherein said acid addition salts are chosen from hydrochloride, hydrobromide, sulphate, tartrate, lactate, and acetate.

36. A composition according to claim 19, wherein said acid addition salts are chosen from hydrochloride, hydrobromide, sulphate, tartrate, lactate, and acetate.

37. A composition according to claim 26, wherein said acid addition salts are chosen from hydrochloride, hydrobromide, sulphate, tartrate, lactate, and acetate.

38. A method for dyeing keratin fibres, comprising:
applying to said keratin fibres for a time sufficient to achieve colour development, a composition comprising:
at least one oxidation base,
at least one cationic direct dye of formula (I) below:

    (I)

wherein:
A is chosen from structures A1, A2, and A3 below:

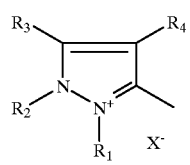 A1

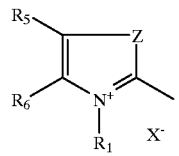 A2

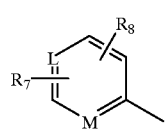 A3 wherein in said structures A1 to A3:
$R_1$ is chosen from $C_1$–$C_4$ alkyl radicals, a phenyl radical, and phenyl radicals having a substituent chosen from $C_1$–$C_4$ alkyl radicals and halogen atoms chosen from chlorine, bromine, iodine and fluorine;
$R_2$ is chosen from $C_1$–$C_4$ alkyl radicals and a phenyl radical;
$R_3$ and $R_4$, which may be identical or different, are chosen from $C_1$–$C_4$ alkyl radicals and a phenyl radical or together form a benzene ring having at least one substituent chosen from $C_1$–$C_4$ alkyl radicals, $C_1$–$C_4$ alkoxy radicals, and nitro radicals; $R_3$ can also be a hydrogen atom;
$R_5$ and $R_6$, which may be identical or different, are chosen from $C_1$–$C_4$ alkyl radicals and a phenyl radical or together form a benzene ring which is unsubstituted or has at least one substituent chosen from $C_1$–$C_4$ alkyl radicals, $C_1$–$C_4$ alkoxy radicals, and nitro radicals; $R_5$ can also be a hydrogen atom;
$R_7$ and $R_8$, which may be identical or different, are chosen from a hydrogen atom, halogen atoms chosen from chlorine, bromine, iodine and fluorine, $C_1$–$C_4$ alkyl radicals, $C_1$–$C_4$ alkoxy radicals and nitro radicals;
Z is chosen from an oxygen atom, a sulphur atom, and a group $NR_2$, wherein $R_2$ is chosen from $C_1$–$C_4$ alkyl radicals and a phenyl radical;
the ring member L is chosen from —CH, —CR and —$N^+R_9(X^-)_r$;
the ring member M is chosen from —CH, —CR and —$N^+R_9(X^-)_r$;
r is an integer equal to 0 or 1;
R is chosen from $C_1$–$C_4$ alkyl radicals;
$R_9$ is chosen from an atom $O^-$, $C_1$–$C_4$ alkyl radicals, and $C_1$–$C_4$ alkoxy radicals;
$X^-$ is chosen from an anion;
with the provisos that:
in said structure A3, at least one of the ring members L and M is a group —$N^+R_9(X^-)_r$;
when $R_6$ is a $C_1$–$C_4$ alkyl radical and Z is a sulphur atom, then $R_5$ is other than a $C_1$–$C_4$ alkyl radical;
when $R_9$ is $O^-$, then r=0;
when L or M is a radical —$N^+R_9(X^-)_r$ wherein $R_9$ is a $C_1$–$C_4$ alkyl radical and r=1, then at least one of the radicals $R_7$ and $R_8$ is other than a hydrogen atom;
when L is a radical —$N^+R_9(X^-)_r$, then M is chosen from —CH and CR;
when M is a radical —$N^+R_9(X^-)_r$, then L is chosen from —CH and CR;
when Z is a group $NR_2$ wherein $R_2$ is a $C_1$–$C_4$ alkyl radical, then at least one of the radicals $R_1$, $R_5$ and $R_6$ is other than a $C_1$–$C_4$ alkyl radical;
B is chosen from:
(a) a group of structure B1 below:

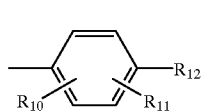 B1 wherein in structure B1,
$R_{10}$ is chosen from a hydrogen atom, halogen atoms chosen from chlorine, bromine, iodine and fluorine, $C_1$–$C_4$ alkyl radicals, $C_1$–$C_4$ alkoxy radicals, a hydroxyl radical, —$NHR_{13}$ groups, —$NR_{14}R_{15}$ groups, —$NHCO(C_1$–$C_4)$alkyl groups and a nitro, or forms with $R_{11}$ a 5- or 6-membered carbon ring or a ring containing at least one hetero atom chosen from nitrogen, oxygen and sulphur;
$R_{11}$ is chosen from a hydrogen atom, halogen atoms chosen from chlorine, bromine, iodine and fluorine, $C_1$–$C_4$ alkyl radicals, and $C_1$–$C_4$ alkoxy radicals or forms with $R_{12}$ or $R_{13}$ a 5- or 6-membered carbon ring or a ring containing at least one hetero atom chosen from nitrogen, oxygen and sulphur;
$R_{12}$ is chosen from a hydrogen atom, a hydroxyl radical, —$NHR_{13}$ radicals, and —$NR_{14}R_{15}$ radicals;
$R_{13}$ is chosen from a hydrogen atom, $C_1$–$C_4$ alkyl radicals, $C_1$–$C_4$ monohydroxyalkyl radicals, $C_2$–$C_4$ polyhydroxyalkyl radicals, and a phenyl radical;
$R_{14}$ and $R_{15}$, which may be identical or different, are chosen from $C_1$–$C_4$ alkyl radicals, $C_1$–$C_4$ monohydroxyalkyl radicals, and $C_2$–$C_4$ polyhydroxyalkyl radicals;
with the provisos that
when Z is a sulphur atom and $R_1$ is a $C_1$–$C_4$ alkyl radical and when one of the radicals $R_{10}$ and $R_{11}$ is a hydrogen atom, then $R_5$ and $R_6$ cannot together form an unsubstituted benzene ring; and
when $R_6$ in structure A2 is a $C_1$–$C_4$ alkyl radical and Z is a sulphur atom and when one of the radicals $R_{10}$ and $R_{11}$ in structure B1 is a hydrogen atom, then $R_5$ is other than a hydrogen atom; and (b) a 5- or 6-membered nitrogenous heterocyclic group, a 5- or 6-membered nitrogenous heterocyclic group comprising at least one additional hetero atom chosen from oxygen and sulphur and/or at least one carbonyl group, wherein said heterocycles are unsubstituted or have at least one substituent chosen from $C_1$–$C_4$ alkyl, amino and phenyl radicals.

39. The method according to claim 38, wherein said composition further comprises an oxidizing agent.

40. The method according to claim 38, wherein said colour is developed at an acidic, neutral, or alkaline pH by an oxidizing agent added sequentially at the time of applying said composition to said fibres, or added simultaneously at the time of applying said composition to said fibres.

41. The method according to claim 38, wherein said keratin fibres are human keratin fibres.

42. The method according to claim 41, wherein said human keratin fibres are human hair.

43. The method according to claim 38, wherein said time sufficient ranges from about 3 to about 50 minues.

44. The method according to claim 43, wherein said time sufficient ranges from about 5 to about 30 minutes.

45. The method according to claim 39, wherein said oxidizing agent present in the composition is chosen from hydrogen peroxide, urea peroxide, alkali metal bromates, persalts, peracids and enzymes.

46. The method according to claim 45, wherein said persalts are chosen from perborates, percarbonates, and persulfates.

47. The method according to claim 39, wherein said oxidizing agent is hydrogen peroxide.

48. A multi-compartment dyeing device or kit for dyeing keratin fibres, comprising at least two separate compartments:
a first compartment comprising an oxidizing composition, and
a second compartment comprising the following composition:
at least one oxidation base,
at least one cationic direct dye of formula (I) below:

$$A\!-\!N\!=\!N\!-\!B \qquad (I)$$

wherein:
A is chosen from structures A1, A2, and A3 below:

A1

A2

-continued

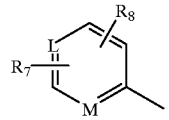
A3 wherein in said structures A1 to A3:
$R_1$ is chosen from $C_1$–$C_4$ alkyl radicals, a phenyl radical, and phenyl radicals having a substituent chosen from $C_1$–$C_4$ alkyl radicals and halogen atoms chosen from chlorine, bromine, iodine and fluorine;
$R_2$ is chosen from $C_1$–$C_4$ alkyl radicals and a phenyl radical;
$R_3$ and $R_4$, which may be identical or different, are chosen from $C_1$–$C_4$ alkyl radicals and a phenyl radical or together form a benzene ring having at least one substituent chosen from $C_1$–$C_4$ alkyl radicals, $C_1$–$C_4$ alkoxy radicals, and nitro radicals; $R_3$ can also be a hydrogen atom;
$R_5$ and $R_6$, which may be identical or different, are chosen from $C_1$–$C_4$ alkyl radicals and a phenyl radical or together form a benzene ring which is unsubstituted or has at least one substituent chosen from $C_1$–$C_4$ alkyl radicals, $C_1$–$C_4$ alkoxy radicals, and nitro radicals; $R_5$ can also be a hydrogen atom;
$R_7$ and $R_8$, which may be identical or different, are chosen from a hydrogen atom, halogen atoms chosen from chlorine, bromine, iodine and fluorine, $C_1$–$C_4$ alkyl radicals, $C_1$–$C_4$ alkoxy radicals and nitro radicals;
Z is chosen from an oxygen atom, a sulphur atom, and a group $NR_2$, wherein $R_2$ is chosen from $C_1$–$C_4$ alkyl radicals and a phenyl radical;
the ring member L is chosen from —CH, —CR and —$N^+R_9(X^-)_r$;
the ring member M is chosen from —CH, —CR and —$N^+R_9(X^-)_r$;
r is an integer equal to 0 or 1;
R is chosen from $C_1$–$C_4$ alkyl radicals;
$R_9$ is chosen from an atom $O^-$, $C_1$–$C_4$ alkyl radicals, and $C_1$–$C_4$ alkoxy radicals;
$X^-$ is chosen from an anion;
with the provisos that:
in said structure A3, at least one of the ring members L and M is a group —$N^+R_9(X^-)_r$;
when $R_6$ is a $C_1$–$C_4$ alkyl radical and Z is a sulphur atom, then $R_5$ is other than a $C_1$–$C_4$ alkyl radical;
when $R_9$ is $O^-$, then r=0;
when L or M is a radical —$N^+R_9(X^-)_r$ wherein $R_9$ is a $C_1$–$C_4$ alkyl radical and r=1, then at least one of the radicals $R_7$ and $R_8$ is other than a hydrogen atom;
when L is a radical —$N^+R_9(X^-)_r$, then M is chosen from —CH and CR;
when M is a radical —$N^+R_9(X^-)_r$, then L is chosen from —CH and CR;
when Z is a group $NR_2$ wherein $R_2$ is a $C_1$–$C_4$ alkyl radical, then at least one of the radicals $R_1$, $R_5$ and $R_6$ is other than a $C_1$–$C_4$ alkyl radical;
B is chosen from:

(a) a group of structure B1 below:

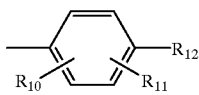

B1 wherein in structure B1, $R_{10}$ is chosen from a hydrogen atom, halogen atoms chosen from chlorine, bromine, iodine and fluorine, $C_1$–$C_4$ alkyl radicals, $C_1$–$C_4$ alkoxy radicals, a hydroxyl radical, —$NHR_{13}$ groups, —$NR_{14}R_{15}$ groups, —$NHCO(C_1$–$C_4)$ alkyl groups and a nitro, or forms with $R_{11}$ a 5- or 6-membered carbon ring or a ring containing at least one hetero atom chosen from nitrogen, oxygen and sulphur;

$R_{11}$ is chosen from a hydrogen atom, halogen atoms chosen from chlorine, bromine, iodine and fluorine, $C_1$–$C_4$ alkyl radicals, and $C_1$–$C_4$ alkoxy radicals or forms with $R_{12}$ or $R_{13}$ a 5- or 6-membered carbon ring or a ring containing at least one hetero atom chosen from nitrogen, oxygen and sulphur;

$R_{12}$ is chosen from a hydrogen atom, a hydroxyl radical, —$NHR_{13}$ radicals, and —$NR_{14}R_{15}$ radicals;

$R_{13}$ is chosen from a hydrogen atom, $C_1$–$C_4$ alkyl radicals, $C_1$–$C_4$ monohydroxyalkyl radicals, $C_2$–$C_4$ polyhydroxyalkyl radicals, and a phenyl radical;

$R_{14}$ and $R_{15}$, which may be identical or different, are chosen from $C_1$–$C_4$ alkyl radicals, $C_1$–$C_4$ monohydroxyalkyl radicals, and $C_2$–$C_4$ polyhydroxyalkyl radicals;

with the provisos that when Z is a sulphur atom and $R_1$ is a $C_1$–$C_4$ alkyl radical and when one of the radicals $R_{10}$ and $R_{11}$ is a hydrogen atom, then $R_5$ and $R_6$ cannot together form an unsubstituted benzene ring; and when $R_6$ in structure A2 is a $C_1$–$C_4$ alkyl radical and Z is a sulphur atom and when one of the radicals $R_{10}$ and $R_{11}$ in structure B1 is a hydrogen atom, then $R_5$ is other than a hydrogen atom; and (b) a 5- or 6-membered nitrogenous heterocyclic group, a 5- or 6-membered nitrogenous heterocyclic group comprising at least one additional hetero atom chosen from oxygen and sulphur and/or at least one carbonyl group, wherein said heterocycles are unsubstituted or have at least one substituent chosen from $C_1$–$C_4$ alkyl, amino and phenyl radicals.

49. A composition according to claim 1, in the form of a liquid, cream, gel, or any other form suitable for dyeing keratin fibres.

* * * * *

UNITED STATES PATENT AND TRADEMARK OFFICE
CERTIFICATE OF CORRECTION

PATENT NO.    : 6,358,286 B2
DATED         : March 19, 2002
INVENTOR(S)   : Gérard Lang et al.

It is certified that error appears in the above-identified patent and that said Letters Patent is hereby corrected as shown below:

Column 23,
Line 16, after "benzene ring", insert -- ; --.

Column 26,
Line 3, after "radicals,", insert a paragraph break; and "-$R_{31}$" should read -- $R_{31}$ --.

Column 35,
In the structure between lines 59-65,

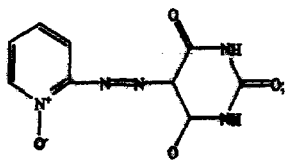 should read -- 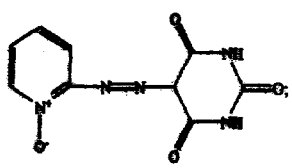 --.

Column 39,
Line 24, "minues" should read -- minutes --.

Column 40,
Line 24, "$R_5$and" should read -- $R_5$ and --.

Signed and Sealed this

Second Day of July, 2002

*Attest:*

*Attesting Officer*

JAMES E. ROGAN
*Director of the United States Patent and Trademark Office*